United States Patent
Urbanski et al.

(10) Patent No.: US 11,501,230 B2
(45) Date of Patent: Nov. 15, 2022

(54) SYSTEMS AND METHODS FOR PERFORMING LOAD OPTIMIZATION OF MEDICATIONS IN AN ELECTRONIC MEDICATION STORAGE CABINET

(71) Applicant: CareFusion 303, Inc., San Diego, CA (US)

(72) Inventors: Christopher Urbanski, Zionsville, IN (US); Crystal Woodward, San Diego, CA (US); Dennis Anthony Tribble, Ormond Beach, FL (US); David D. Swenson, Encinitas, CA (US); Francisco Jose Cuesta De Pablo, Vista, CA (US)

(73) Assignee: CAREFUSION 303, INC., San Diego, CA (US)

( * ) Notice: Subject to any disclaimer, the term of this patent is extended or adjusted under 35 U.S.C. 154(b) by 175 days.

(21) Appl. No.: 16/907,072

(22) Filed: Jun. 19, 2020

(65) Prior Publication Data
US 2020/0401973 A1 Dec. 24, 2020

Related U.S. Application Data

(60) Provisional application No. 62/865,048, filed on Jun. 21, 2019.

(51) Int. Cl.
*G06Q 10/08* (2012.01)
*G16H 40/20* (2018.01)
(Continued)

(52) U.S. Cl.
CPC ....... *G06Q 10/06316* (2013.01); *A47B 67/02* (2013.01); *G05B 15/02* (2013.01);
(Continued)

(58) Field of Classification Search
CPC ............... G07F 17/0092; G07F 11/62; G06Q 30/0639; G06Q 10/087; G16H 20/13; G16H 40/20; A61G 12/001
USPC .................................................. 700/236, 242
See application file for complete search history.

(56) References Cited

U.S. PATENT DOCUMENTS 5,905,653 A  5/1999  Higham et al.
6,116,461 A *  9/2000  Broadfield .......... G07F 17/0092
                                                            221/98

(Continued)

OTHER PUBLICATIONS

International Search Report and Written Opinion for Application No. PCT/US2020/038842, dated Sep. 11, 2020, 17 pages.

*Primary Examiner* — Timothy R Waggoner
(74) *Attorney, Agent, or Firm* — Morgan, Lewis & Bockius LLP

(57) ABSTRACT

An electronic medication storage cabinet includes a plurality of drawers configured with a plurality of sensors arranged to identify a positioning of storage pockets within the drawers. Upon receiving an indication of a new medicine container to be loaded in the cabinet, a sequence of steps to load the medicine container into the cabinet is generated based on a mapping algorithm. A first step is displayed on a display the cabinet, and a determination is made as to whether the first step is associated with one of the plurality of drawers. In response to determining that the first step is associated with one of the plurality of drawers, the drawer is automatically unlocked. In response to determining that the first step is successfully completed, a determination of whether execution of any additional steps is pending and indicated on the display.

20 Claims, 10 Drawing Sheets

(51) Int. Cl.
  *G06Q 10/06* (2012.01)
  *G07C 9/38* (2020.01)
  *A47B 67/02* (2006.01)
  *G05B 15/02* (2006.01)
  *G06F 21/30* (2013.01)
  *G07C 9/00* (2020.01)

(52) U.S. Cl.
  CPC ........... *G06F 21/30* (2013.01); *G06Q 10/087* (2013.01); *G07C 9/00571* (2013.01); *G07C 9/38* (2020.01); *G16H 40/20* (2018.01); *A47B 2067/025* (2013.01)

(56) References Cited

U.S. PATENT DOCUMENTS

| | | | |
|---|---|---|---|
| 7,177,721 B2 * | 2/2007 | Kirsch | G07F 17/0092 700/242 |
| 8,332,066 B2 * | 12/2012 | Weber | G07F 11/62 700/242 |
| 2006/0058918 A1 * | 3/2006 | Handfield | A61J 7/0084 700/236 |
| 2007/0135965 A1 * | 6/2007 | Nguyen | G16H 20/13 700/231 |
| 2007/0288296 A1 * | 12/2007 | Lewis | G06Q 30/02 186/52 |
| 2008/0319790 A1 * | 12/2008 | Vahlberg | G16H 20/13 705/2 |
| 2010/0030667 A1 | 2/2010 | Chudy et al. | |
| 2011/0054668 A1 | 3/2011 | Holmes et al. | |
| 2012/0253510 A1 | 10/2012 | Thomas et al. | |
| 2013/0082581 A1 | 4/2013 | Bufalini et al. | |
| 2015/0324725 A1 * | 11/2015 | Roesbery | G06Q 30/0639 705/7.39 |
| 2017/0053099 A1 | 2/2017 | Coughlin et al. | |

\* cited by examiner

SYSTEMS AND METHODS FOR PERFORMING LOAD OPTIMIZATION OF MEDICATIONS IN AN ELECTRONIC MEDICATION STORAGE CABINET

CROSS REFERENCE TO RELATED APPLICATIONS

This application claims the benefit as a nonprovisional of U.S. Provisional Application Ser. No. 62/865,048, entitled "SYSTEMS AND METHODS FOR PERFORMING LOAD OPTIMIZATION OF MEDICATIONS IN AN ELECTRONIC MEDICATION STORAGE CABINET," filed on Jun. 21, 2019, the entirety of which is incorporated herein by reference.

TECHNICAL FIELD

This application relates generally to optimizing space within a device, such as an electronic medication storage cabinets used in healthcare organizations.

BACKGROUND

Medication dispensing cabinets are frequently utilized in hospitals to serve multiple patients. Prescription medication may be placed in such dispensing cabinets. Periodically the medications stored in the cabinet may be updated to assure that medications commonly prescribed by physicians are available as prescribing patterns often change over time. When this occurs medication are removed from the dispensing cabinets to make room for other medications. However, it is often difficult to gauge how much space a particular medication will require, as well as how much space is available in the medication dispensing cabinets. With differing sizes of medications, drawers, and storage compartments within the drawers, it becomes time consuming to organize items to create adequate storage space.

Pharmacists, nurses, and other operators of the dispensing cabinets often struggle to place critical medications in cabinets that are close to full capacity. Thus, with the ever-growing need for quick, efficient, and reliable access to medication for patients, the need to efficiently place and locate medication has increased. Methods of optimizing available storage space for patient medication are desired.

SUMMARY

Typically, a user, such as a pharmacy technician, when placing or loading new medications into to an electronic medication storage unit, such as an automated medication dispensing cabinet, reconfigures the electronic medication storage unit. However, the user, at the time of loading the medications into the electronic medication storage unit does not have the necessary tools to optimize the contents of the electronic medication storage unit.

Accordingly, there is a need for methods and systems that can optimize the space of an electronic medication storage unit having predefined storage capabilities and requirements, and to guide a user through the steps to optimally load the medication into the electronic medication storage unit. Disclosed implementations are able to efficiently provide optimization instructions for use in a healthcare organization.

In accordance with some implementations, a method includes providing an electronic medication storage unit comprising a plurality of drawers, each drawer configured with a plurality of storage pockets, the drawer configured with a plurality of sensors arranged to identify a positioning of the plurality of storage pockets within the drawer. The method includes receiving an indication of a new medicine container to be loaded in the electronic medication storage unit. The method includes displaying a first step of a sequence of one or more steps to load the medicine container into an electronic medication storage cabinet on a display on the electronic medication storage cabinet, wherein the sequence is generated based on a mapping algorithm. The method includes determining whether the first step of the sequence of the one or more steps is associated with one of the plurality of drawers. The method includes, in response to determining that the first step is associated with one of the plurality of drawers, automatically unlocking the associated drawer. The method includes determining whether the first step is successfully completed. The method includes, in response to determining that the first step is successfully completed, determining whether execution of any additional steps is pending. The method includes generating an alert in response to determining that execution of no additional steps is pending. Other aspects include corresponding systems, apparatus, and computer program products for implementation of the method.

In accordance with some implementations, a method includes providing an electronic medication storage cabinet having a plurality of drawers, each drawer configured with a plurality of removable storage pockets, the drawer configured with a plurality of sensors arranged to identify a positioning of the plurality of removable storage pockets within the drawer. The method includes receiving an indication of a new medicine container to be stored in the electronic medication storage cabinet which requires a new storage pocket to be added to the electronic medication storage cabinet. The method further includes determining, based on receiving the indication, that at least a subset of removable storage pockets within one or more of the plurality of drawers require repositioning to accommodate the new pocket. The method further comprises generating, based on a mapping algorithm, a new arrangement of the subset of removable storage pockets and the new pocket within the one or more of the plurality of drawers. At the electronic medication storage cabinet, execute a predetermined sequence of steps for effecting the new arrangement including: (1) automatically unlocking a first drawer of the plurality of drawers, (2) providing a first prompt to remove at least a first storage pocket of the subset of removable storage pockets, (3) verifying, via the plurality of sensors, that the first storage pocket was removed, (4) providing a second prompt to relocate the first pocket within a first available space within the one or more of the plurality of drawers, (5) verifying, via the plurality of sensors, that the first pocket was relocated, (6) providing a third prompt to insert the new pocket within a second available space of the one or more of the plurality of drawers, and (7) verifying, via the plurality of sensors, that the new pocket was inserted. Other aspects include corresponding systems, apparatus, and computer program products for implementation of the method.

In accordance with some implementations, an electronic medication storage cabinet includes one or more processors and memory storing one or more programs configured for execution by the one or more processors. The one or more programs include instructions for performing the operations of any of the methods described in this application. In accordance with some implementations, a non-transitory computer-readable storage medium stores instructions that, when executed by a server system, cause the server system to perform the operations of any of the methods described in this application.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

It will also be understood that, although the terms "first" and "second" are used herein to describe various elements, these elements should not be limited by these terms. These terms are used only to distinguish one element from another. For example, a first drawer could be termed a second drawer, and, similarly, a second drawer could be termed a first drawer, without departing from the scope of the various described implementations. The first drawer and the second drawer are both drawers, but they are not the same drawer.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof.

Figure 1A:
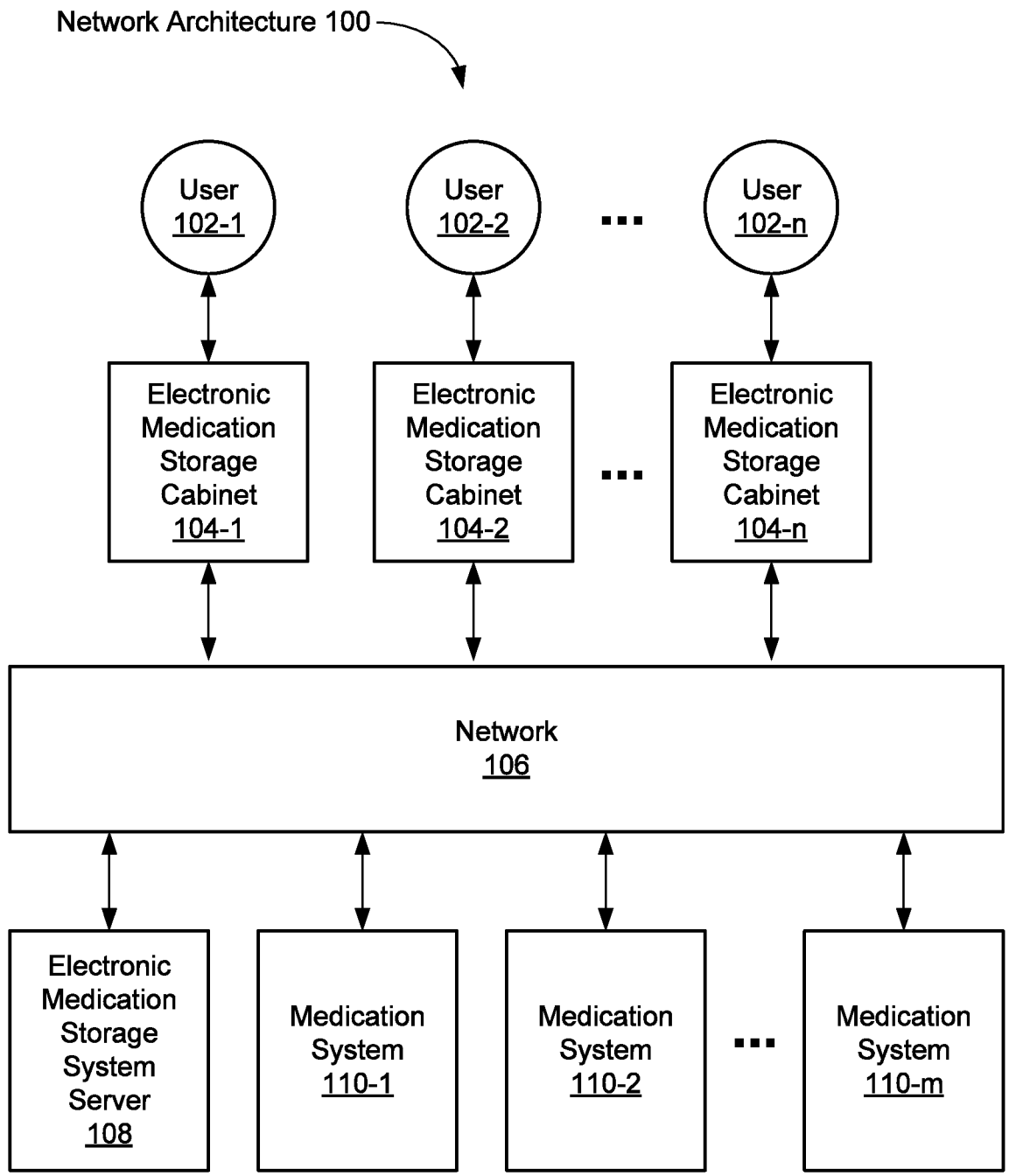
FIG. 1A is a block diagram of a network architecture for load optimization of medication into electronic medication storage unit according to illustrative implementations.

FIG. 1 is a block diagram of a network architecture 100 in accordance with some embodiments.

The network architecture 100 includes one or more electronic medication storage cabinets 104-1, 104-2, . . . , 104-n, collectively referred to herein as electronic medication storage cabinets 104. In some implementations, an electronic medication storage cabinet 104 may be communicatively and/or operably coupled to one or more other electronically controlled and/or managed medication storage units, such as electronically controlled and/or managed medication storage towers, electronically controlled and/or managed medication storage refrigerators, and the like.

The one or more electronic medication storage cabinets 104 may be communicatively coupled to an electronic medication storage system server 108 by one or more communication networks 106. The electronic medication storage system server 108 may be communicatively coupled to one or more patient and/or medication related systems 110-1, 110-2, . . . , 110-m, collectively referred to herein as medication systems 110, by one or more communication networks 106. The one or more medications systems 110 may be any system configured to store, maintain, and/or update data related to active and/or discharged patients, locations of the patients (e.g., within a healthcare facility), medication orders for the patients, and the like. Examples of medication systems 110 include, but are not limited to, an electronic medical record system, a pharmacy information system, and the like. In some implementations, the electronic medication storage cabinets 104 may be communicatively coupled to the medication systems 110 via the electronic medication storage system server 108. In some implementations, the electronic medication storage cabinets 104 may be communicatively coupled to the medication systems 110 by the one or more communication networks 106.

Examples of the one or more communication networks 106 include, but are not limited to, an intranet, the Internet, cellular telephone networks, mobile data networks, wide area networks, local area networks, metropolitan area networks, and the like. In some implementations, the one or more communication networks 106 include a public communication network (e.g., the Internet and/or a cellular data network), a private communications network (e.g., a private LAN or leased lines), or a combination of such communication networks. The electronic medication storage cabinets 104 may be configured to communicate with the electronic medication storage system server 108 and/or the medication systems 110. In some implementations, the electronic medication storage cabinets 104 may be configured to receive and/or transfer patient and/or medication related data from the electronic medication storage system server 108 or medication systems 110. Examples of patient related data include, but are not limited to, patient biographical information, electronic medical records, information related to one or more recent procedures or treatment, information related to any prescribed medication, and the like. Examples of medication related data include, but are not limited to, medications stored in the electronic medication storage cabinets 104, location of medications stored in the electronic medication storage cabinets 104, and the like.

In some implementations, the electronic medication storage system server 108 is a single computing device such as a computer server, while in other implementations, the electronic medication storage system server 108 is implemented by multiple computing devices working together to perform the actions of a server system (e.g., cloud computing). Additional details of the electronic medication storage system server 108 are described herein and with reference to FIG. 2.

The electronic medication storage cabinets 104 may include one or more input devices (shown in FIG. 3) configured to receive inputs to the electronic medication storage cabinets 104. The users 102-1, 102-2, ..., 102-n, collectively referred to herein as users 102, may interact with the one or more electronic medication storage cabinets 104 via the one or more input devices. The users 102 may utilize the electronic medication storage cabinets 104 to access the electronic medication storage system server 108 and/or medication systems 110 to participate in corresponding services provided by the electronic medication storage system server 108 and/or medication systems 110.

Figure 1B:
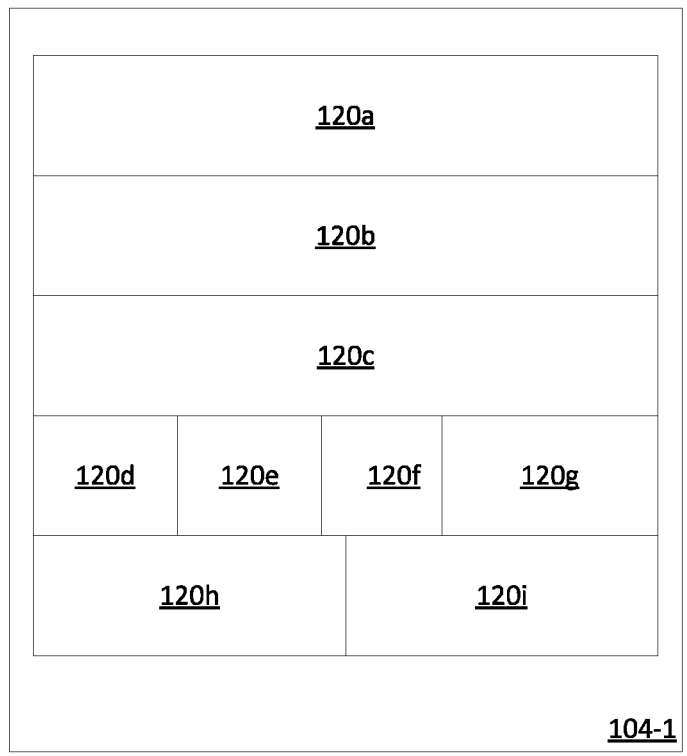
FIG. 1B is a front view of an electronic medication storage cabinet according to illustrative implementations.

The electronic medication storage cabinets 104 may include one or more electronically controlled and/or managed movable drawers. For example, as shown in FIG. 1B, the electronic medication storage cabinet 104-1 includes electronically controlled and/or managed movable drawers 120a, 120b, 120c, 120d, 120e, 120f, 120g, 120h, 120i, collectively referred to herein as movable drawers 120. FIG. 1B is a front view of the electronic medication storage cabinet 104-1. In some implementations, some movable drawers 120 may be of different sizes. In some implementations, the electronic medication storage cabinets 104 may be configured to associate one or more movable drawers 120 with one or more patients. For example, the electronic medication storage cabinet 104-1 may be configured to associate movable drawer 120a with a first patient, and movable drawer 120c with a second patient. In some implementations, the electronic medication storage cabinets 104 may be configured to associate one movable drawer 120 with multiple patients. For example, the electronic medication storage cabinet 104-1 may be configured to associate movable drawer 120c with the second patient and a fourth patient. In some implementations, the electronic medication storage cabinets 104 may be configured to associate a patient with one or more movable drawers 120 based on the medications stored in a movable drawer 120. For example, if a patient is prescribed a medication or is associated with a medication, the electronic medication storage cabinet 104 may be configured to associate the patient with a drawer that comprises the prescribed medication.

The movable drawers 120 may include or be configured with one or more sensor devices (not shown in FIG. 1B). For example, movable drawers 120 may be configured with sensor devices on the inside portions of the floors of the movable drawers 120. In some implementations, the sensor devices may be placed in one or more patterns at different locations within the movable drawers 120. Examples of such patterns include, but are not limited to, grid patterns, and the like. In some implementations, the sensor devices may be placed in a grid pattern covering a major portion of the movable drawers 120. For example, the sensor devices may be placed in a grid pattern covering at least a majority of the inside floor of the movable drawers 120.

Figure 1C:
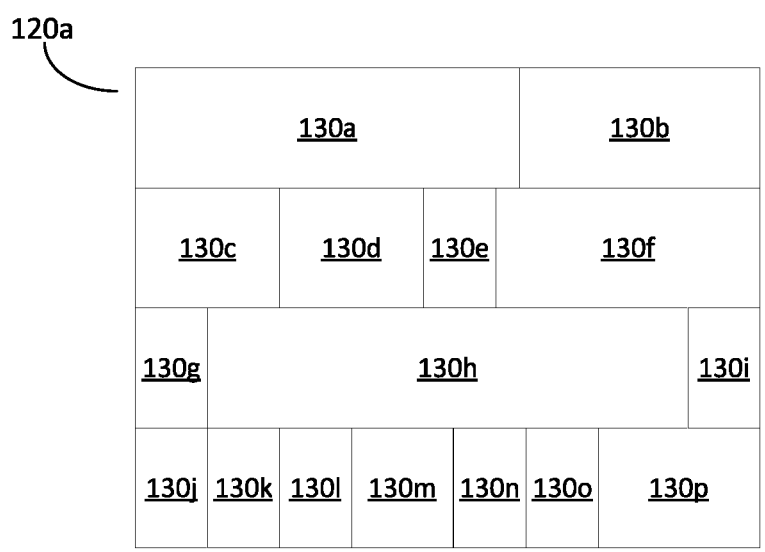
FIG. 1C is top view of a drawer of an electronic medication storage cabinet according to illustrative implementations.

Each movable drawer 120 may have one or more pockets. For example, as shown in FIG. 1C, the movable drawer 120a includes pockets 130a, 130b, 130c, 130d, 130e, 130f, 130g, 130h, 130i, 130j, 130k, 1301, 130m, 130n, 130o, and 130p, collectively referred to herein as pockets 130. FIG. 1C is a top view of the movable drawer 120a. In some implementations, the pockets 130 may be different sizes and shapes. In some implementations, one or more pockets 130 may be fixed to a particular location within the movable drawer 120. Such pockets 130 are referred to herein as fixed pockets. In some implementations, one or more pockets 130 may be movable from a first location within the movable drawer 120 to a second location within the movable drawer 120, and/or relocated to a different movable drawer 120 within the same cabinet also configured for movable pockets, and/or removed from the movable drawer 120. Such pockets 130 may be referred to herein as dynamic pockets. In some implementations, a dynamic pocket may be moved to a drawer of another cabinet configured for movable pockets. In some implementations, contents of a pocket 130 of one type (e.g., dynamic or fixed) may be transferred to a pocket of the other type (e.g., fixed or dynamic) in the same cabinet. For example, the contents of a fixed type pocket 130 may be transferred to a dynamic type pocket 130. Similarly, the contents of a dynamic type pocket 130 may be transferred to a fixed type pocket 130.

The pockets 130 may include or be configured with transmitter devices (not shown in FIG. 1B). In some implementations, the transmitter devices of the pockets 130 may be light based transmitter devices (e.g., laser based transmitter, and the like). In some implementations, the pockets 130 may include radio-frequency identification (RFID) based electronic devices (e.g., RFID tags).

In some implementations, pockets 130 may be either assigned to contain a single medication for use by multiple patients ("medication-specific"), a plurality of medications for use by a specific patient ("patient-specific"), or a single medication which may be a controlled substance for use only by a specific patient ("patient-specific controlled substance").

Figure 2:
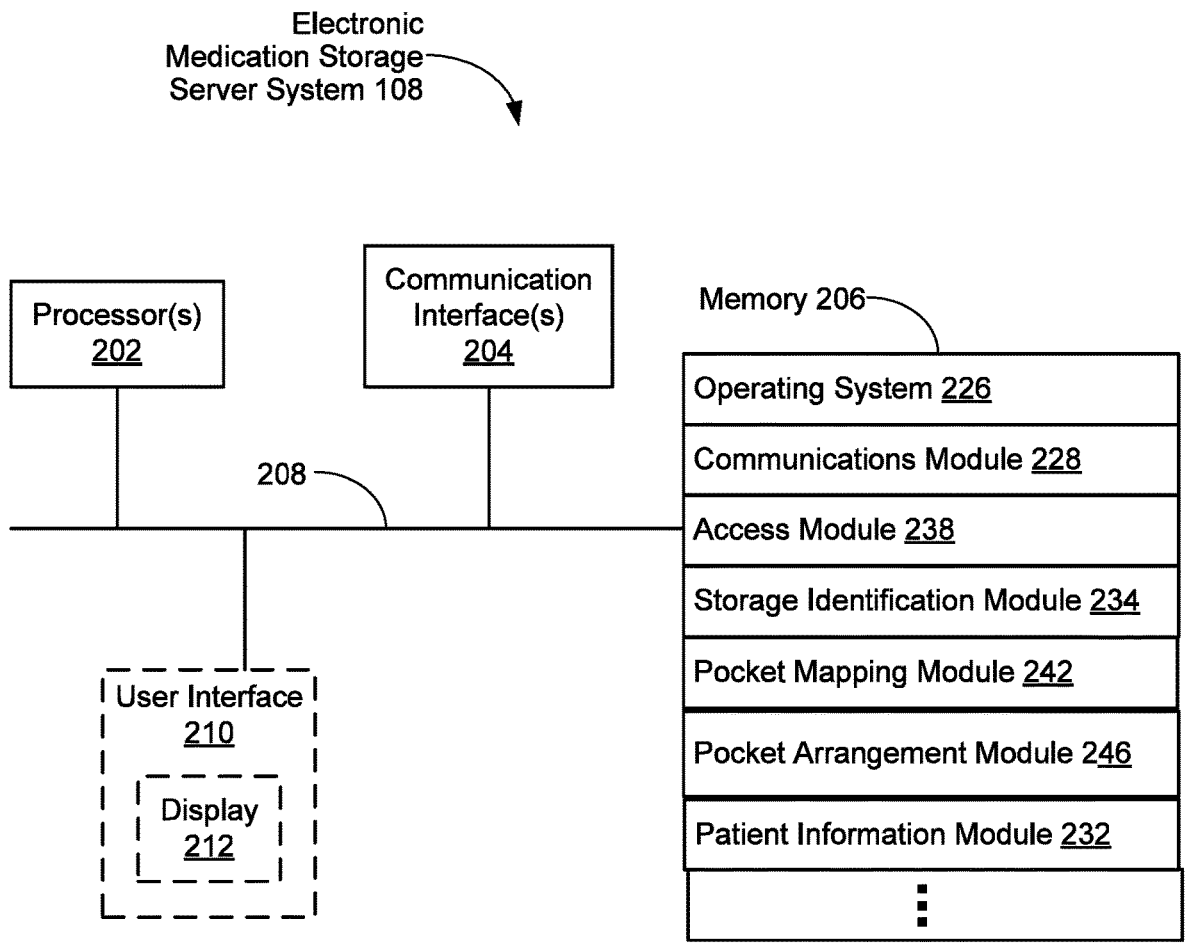
FIG. 2 is a block diagram of an exemplary server system from the architecture of FIG. 1 according to illustrative implementations.

Turning now to FIG. 2, there is shown a block diagram depicting an electronic medication storage system server 108 in accordance with some implementations. The electronic medication storage system server 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. In some implementations, the electronic medication storage system server 108 may include a display device 212. In some implementations, the electronic medication storage system server 108 may include input devices such as a keyboard, a mouse, a trackpad, and/or input buttons. In some implementations, the display device 212 may include a touch-sensitive surface, in which case the display is a touch-sensitive display.

In some implementations, the electronic medication storage system server 108 may be configured to receive data related to patients, pockets 130, movable drawers 120, and the like, from the electronic medication storage cabinets 104. In some implementations, the electronic medication storage system server 108 may be configured to transmit data related to optimized processes of loading ordered medications to electronic medication storage cabinets 104. The electronic medication storage system server 108 may be configured to receive data related to ordered medications for patients, for loading into electronic medication storage cabinets 104, and the like, from medication systems 110. The electronic medication storage system server 108 may be configured to transmit data related to dispensing of medication in medication containers, status indicating success or failure of loading the ordered medications into the electronic medication storage cabinets 104, and the like, to the medication systems 110. In some implementations, the electronic medication storage system server 108 may be located either on premises of a healthcare organization, remotely hosted by a third-party service provider (e.g., in a cloud computing environment), and/or a combination thereof.

The electronic medication storage system server 108 may be configured with a mapping algorithm that is configured to identify a location in an electronic medication storage cabinet to store a medication and/or a medicine container containing the medication. In some implementations, the medicine container may be a dynamic pocket described herein. The one or more processes of the mapping algorithm are described herein with reference to FIGS. 4A-4D. The electronic medication storage system server 108 may generate a sequence of one or more steps to load the medication and/or the medicine container into the identified location of an electronic medication storage cabinet based on the mapping algorithm.

The memory 206 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures that may be used for the performing one or more operations of the server system 108. The electronic storage system server 108 may execute the mapping algorithm based on one or more modules described herein and/or included in the memory 206. For example, the memory 206 may include programs, modules, and/or data structures for an operating system 226, a network communication module 228, a patient information module 232, an access device module 238, a storage identification module 234, a pocket mapping module 242, a pocket arrangement module 246.

In some implementations, the operating system 226 module may include procedures for handling various basic system services and for performing hardware dependent tasks. The network communication module 228 may be configured for connecting the server system 108 to other computing devices via the one or more communication network interfaces 204 (wired or wireless) and one or more communication networks 106. The patient information module 232 may be configured to store data related to patients including, but not limited to, medical history, prescription medication, allergies, and the like. The patient information module 232 may be configured to associate a patient with an electronic medication storage cabinet 104, and store the association in memory 206. The access module 238 may be configured to grant, deny, and/or modify access to the server system 108 and/or one or other computing systems or devices communicatively coupled to the server system 108.

The storage identification module 234 may be configured to store, maintain, and/or update data related to the contents of every pocket 130 for each electronic medication storage cabinet 104 communicatively coupled to the electronic medication storage system server 108. The storage identification module 234 may be configured to store, maintain, and/or update data related to every empty pocket 130 for each electronic medication storage cabinet 104 communicatively coupled to the electronic medication storage system server 108. The electronic medication storage system 108 may receive data related to contents of pocket 130 from the electronic medication storage cabinets 104, and the storage identification module 234 may be configured to maintain and/or update data related to contents of pocket 130 based on the data received from the electronic medication storage cabinets 104. In some implementations, storage identification module 234 may be similarly configured as storage identification module 334 described below with reference to FIG. 3.

For each electronic medication storage cabinet 104 communicatively coupled to the electronic medication storage system server 108, the pocket mapping module 242 may be configured to associate the dynamic and/or fixed pockets 130 of each movable drawer 120 with corresponding locations in the movable drawer 120, and store the associations in memory 206. In some implementations, the pocket mapping module 242 may be configured to receive data related to sensors with their locations in drawers 120 for each electronic medication storage cabinet 104, and based on the mapping, the pocket mapping module 242 may be configured to determine locations of pockets within the drawers 120. In some implementations, the pocket mapping module 242 may be similarly configured as the pocket mapping module 342 described below with reference to FIG. 3.

The pocket arrangement module 246 may be configured to determine processes to rearrange one or more dynamic pockets 130 in the electronic medication storage cabinets 104 based on dimensions and/or size of other dynamic pockets 130 in the electronic medication storage cabinets 104 and/or a new dynamic pocket 130 comprising a newly ordered medication. The pocket arrangement module 246 may be similarly configured as pocket arrangement module 346 described below with reference to FIG. 3.

Each of the above identified modules and applications corresponds to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various implementations. In some implementations, the memory 206 may store a subset of the modules and data structures identified above. In some implementations, the memory 206 may store additional modules and data structures not described above. Processors 202 may be configured to execute the above identified modules for performing the one or more above-described functions and/or techniques of optimizing loading of medications in electronic medication storage cabinet 104 as described herein with reference to FIGS. 4A-4D.

Figure 3:
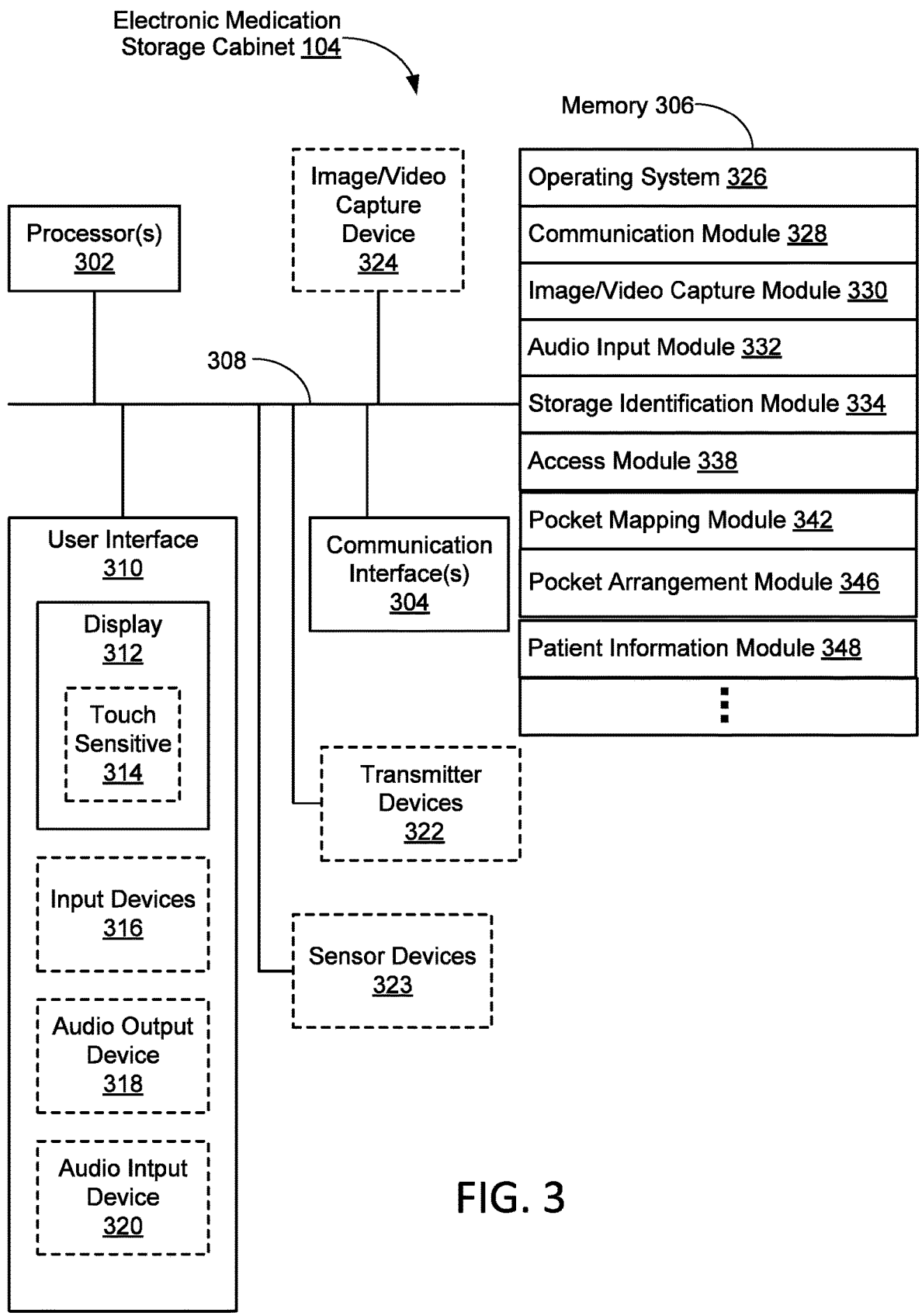
FIG. 3 is a block diagram of an exemplary client device from the architecture of FIG. 1 according to illustrative implementations.

Turning now to FIG. 3, there is shown a block diagram depicting an electronic medication storage cabinet 104. An electronic medication storage cabinet 104 may include one or more processors 302, one or more network or communications interfaces 304, memory 306, one or more communication buses 308, a user interface unit 310, transmitter devices 322, sensor devices 323. The one or more processors 302, the one or more network or communication interfaces 304, memory 306, and the user interface unit 310 may be configured to communicate with one another via the one or more communication buses 308. In some implementations, the communication buses 308 may include circuitry (sometimes called a chipset) that interconnects and controls communications between components of the electronic medication storage cabinet 104. In some implementations, the electronic medication storage cabinet 104 may include an image/video capture device 324, such as a camera.

In some implementations, the electronic medication storage cabinet 104 may be configured with the mapping algorithm, and one or more processors 302 of the electronic medication storage cabinet 104 may be configured to identify a location in the electronic medication storage cabinet 104 to store a medication and/or a medicine container containing the medication. In some implementations, the medicine container may be a dynamic pocket described herein. As described above, the one or more processes of the mapping algorithm are described herein with reference to FIGS. 4A-4D. The electronic medication storage cabinet 104 may generate a sequence of one or more steps to load the medication and/or the medicine container into the identified location of an electronic medication storage cabinet based on the mapping algorithm.

The user interface unit 310 may include a display 312, one or more input devices 316, such as a keyboard or a mouse, one or more audio output devices 318, and/or one or more audio input devices 320. In some implementations, the display 312 may include a touch sensitive display or surface 314, which is configured to receive inputs from a user 102. The one or more audio output devices 318 may include, but are not limited to, speakers, interfaces configured to transfer audio related data to a device configured to project audio, and the like. The one or more input devices 320 may include, but are not limited to, microphones, interfaces configured to receive audio related data from a device configured to receive audio.

The movable drawers 120 of the electronic medication storage cabinet 104 may include or be configured with one or more sensor devices, such as sensor devices 323. For example, movable drawers 120 may be configured with sensor devices 323 on the inside portions of the floors of the movable drawers 120. In some implementations, the sensor devices may be placed in one or more patterns at different locations within the movable drawers 120. Examples of such patterns include, but are not limited to, grid patterns, and the like. In some implementations, the sensor devices may be placed in a grid pattern covering a major portion of the movable drawers 120. For example, the sensor devices may be placed in a grid pattern, forming a grid array of sensors, covering at least a majority of the inside floor of the movable drawers 120. In some implementations, the sensor devices 323 may be placed around a perimeter of the movable drawer 120 such that they from a grid of light or signals.

The pockets 130 may include or be configured with transmitter devices, such as transmitter devices 322. In some implementations, the transmitter devices 322 may be light based transmitter devices (e.g., laser based transmitter, and the like). In some implementations, the transmitter devices 322 may be radio-frequency identification (RFID) based devices (e.g., RFID tags).

The sensor devices 323 may be configured to receive signals from the transmitter devices 322 and output signals based on signals received from transmitter devices 322. For example, a sensor device 323 may be configured to detect whether a transmitter device 322 is placed near the sensor device 323 based on a signal received from the transmitter device 322 and produce a signal indicating that a pocket associated with that transmitter device 322 is placed near that sensor device 323.

The one or more modules (e.g. the pocket mapping module 342) described herein, and/or processor 302, may be configured to determine a location of a pocket 130 within the electronic medication storage cabinet 104 based on the signals or output data from sensors 323. For example, if the sensor devices 323 are placed in a grid pattern, forming a grid array of sensors, in a movable drawer 120, then based on sensor devices 323 in the grid pattern that detect a signal from the transmitter device associated with the pocket 130, the one or more modules (e.g., the pocket mapping module 342) may be configured to determine the location of the pocket 130 on the grid array of sensor devices 323 and within the drawer 120. Similarly, based on the signals or output data from the sensor devices 323, the one or more modules (e.g. the pocket mapping module 342) may be configured to determine if a pocket 130 has been removed from its current location within the electronic medication storage cabinet 104. Similarly, based on the signals or output data from the sensor devices 323, the one or more modules (e.g. the pocket mapping module 342) may be configured to determine if a pocket 130 has been placed in a certain or new location within the electronic medication storage cabinet 104.

The memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processor(s) 302. The memory 306, or alternatively the non-volatile memory device(s) within the memory 306, includes a non-transitory computer-readable storage medium. In some implementations, the memory 306 or the computer-readable storage medium of the memory 306 stores the programs, modules, and data structures that may be used for performing operations of the electronic medication storage cabinets 104 and for performing techniques described herein for optimization of loading or one or more medications into an electronic medication storage cabinet. In some implementations, the electronic storage cabinet 104 may execute the mapping algorithm based on one or more modules described herein and/or included in the memory 306. The memory 306 may include an operating system 326, a network communication module 328, an image/video capture module 330, an audio input/output module 332, a storage identification module 334, an access module 338, a pocket mapping module 342, a pocket arrangement module 346, and/or a patient information module 348.

The operating system 326 may be configured to perform procedures of execution of various system services of the electronic medication storage cabinet 104, including, but not limited to, hardware, and software dependent tasks. The network communication module 328 may be configured to execute instructions to connect the electronic medication storage cabinet 104 to one or more other computing devices, such as the healthcare server system 108, third party servers 110, and the like, via the one or more communication interfaces 304 and communication networks, such as the communication network 106. The image/video capture module 330 may be configured to execute instructions to capture images or a continuous stream of images. The audio input module 332 may be configured process received input data and transmit instructions and/or related data to one or more other components of the electronic medication storage cabinet 104. The access module 338 may be configured grant, deny, and/or modify access to the electronic medication storage cabinet 104. For example, the access module 338 may be configured to grant or deny access to the electronic medication storage cabinet 104 based on received login credentials for the electronic medication storage cabinet 104.

The storage identification module 334 may be configured for storing a list of empty pockets 130 within the electronic medication storage cabinet 104. In some implementations, each of the pockets 130 within the electronic medication storage cabinet 104 may be associated with a unique identifier and the storage identification module 334 may be configured to generate and/or update the list of empty pockets with the unique identifiers of the pockets 130 that are empty. As described above, the pockets 130 may include transmitter devices 322 that are RFID tags, and in some implementations, the RFID tag of the pocket may include data related to medication within the pocket 130.

The pocket mapping module 342 may be configured to associate the dynamic and/or fixed pockets 130 of the electronic medication storage cabinet 104 with locations within a movable drawer 120. In some implementations, the pocket mapping module 342 may be configured to use data from sensor devices 323 located within drawers 120, and/or data from transmitter devices 322 included within or configured with pockets 130 to determine locations of the pockets 130 within movable drawers 120. In some implementations, the pocket mapping module 342 may be configured to associate a pocket 130 with one or more nearby sensor devices in response to the pocket 130 being placed at a particular location within the drawer 120.

In some implementations, the pocket mapping module 342 may be configured to generate a mapping of the sensors with their particular location within the drawer 120, and based on the mapping, the pocket mapping module 342 may be configured to determine the location of a particular pocket within the drawer 120. For example, a subset of sensor devices 323 of the electronic medication storage cabinet 104-1 may be located within a movable drawer 120a, and the pocket mapping module 342 may be configured to determine the location of pocket 130d based on one or more sensor devices 323 associated with pocket 130d and the mapping of the associated sensor devices 323 with location of the removable drawer 120a. The pocket mapping module 342 may be configured to map a medication with a pocket in which it is stored and store the mapping of the medications to pockets in data storage unit.

The pocket arrangement module 346 may be configured to rearrange pockets 130 within the electronic medication storage cabinet 104 based on dimensions and/or size of a new pocket 130 and/or ordered medication. The pocket arrangement module 346 may be configured to identify one or more dynamic pockets in the electronic medication storage cabinet 104, which when rearranged to other drawers 120 or within the same drawer 120 will create sufficient contiguous space in one of the drawers 120 to place the new dynamic pocket 130. For example, based on dimensions and/or size of a new dynamic pocket 130, the pocket arrangement module 346 may identify pocket 130e and 130f in drawer 120a that if moved to a different drawer 120 (e.g., 120b, 120c) will create sufficient space within the first drawer 120a for the new pocket 130. Continuing with the example, for each of the identified pockets 130e and 130f, the pocket arrangement module 346 may be configured to determine, based on their respective dimensions and/or size, if sufficient contiguous space is available within the other drawers of the electronic medication storage cabinet 104 to successfully move the pockets 130e and 130f from the drawer 120a a to the other drawers. In some implementations, in response to determining that the identified pockets may be successfully moved to other drawers, the pocket arrangement module 346 may send a message to the one or more processors 302 indicating that one or more pockets 130 can be rearranged to create sufficient contiguous space for the new pocket 130.

The patient information module 348 may be configured to store, and/or access patient data of patients associated with the electronic medication storage cabinet 104. The patient information module 348 may be configured to store data in and/or access patient data from a data storage unit of the electronic medication storage cabinet 104 or operably coupled to the electronic medication storage cabinet 104. Additional details of the load optimization steps and/or techniques are described herein with reference to FIGS. 4A-4D.

Each of the above identified modules and applications corresponds to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various implementations. In some implementations, the memory 206 and/or the memory 306 store a subset of the modules and data structures identified above. In some implementations, the memory 206 and/or the memory 306 stores additional modules and data structures not described above. Processors 302 may be configured to execute the above identified modules for performing the one or more above-described functions and/or techniques of optimizing loading of medications in an electronic medication storage cabinet as described herein with reference to FIGS. 4A-4D.

Turning now to FIGS. 4A-4D, there are shown flowcharts illustrating an optimized process of identifying a location to store a medication in an electronic medication storage cabinet. For the purpose of illustrating a clear example, components of the network architecture 100, shown and described with reference to FIG. 1, components of the electronic medication storage system server 108, shown and described with reference to FIG. 2, and components of the electronic medication storage cabinets 104, shown and described with reference to FIG. 3, may be used to describe the optimized process of loading a medication in an electronic medication storage cabinet 104. In some implementations, the optimized process of loading a medication in an electronic medication storage cabinet 104 described herein with reference to FIGS. 4A-4D may be performed and/or executed by electronic medication storage system server 108 via processors 202 and its modules, and in some implementations, by electronic medication storage cabinet 104 via processors 302 and its modules.

The method 400 includes receiving, by one or more processors 202 of the electronic medication storage system server 108, an order for a medication (block 401). The order for the medication may be received via a message from a medication system 110. As described above, a medication system 110 may be a medication ordering system and/or a medication prescribing system, such as an electronic medical record system, a pharmacy information system, and the like, of a medical facility, such as a hospital. In some implementations, the processors 202 may be configured to determine, via the patient information module 232, whether the medication is ordered for a patient associated with an electronic medication storage cabinet 104. The one or more processors 202 may be configured to determine whether the ordered medication is chosen (e.g., by a user) to be loaded in the electronic medication storage cabinet 104 (block 402). The one or more processors 202 may be configured to determine whether the ordered medication is chosen to be loaded in the electronic medication storage cabinet 104 based on a received message specifying the ordered medication. The received message may specify the choice of a user, such as a pharmacist or a pharmacist technician, of a medication system 110 to load the ordered medication into the electronic medication storage cabinet 104. The user of the medication system 110 may provide the choice to load the ordered medication via an input to the medication system 110, and the medication system 110 may include information related to the choice in the message received by the medication storage cabinet 104. For example, the received message specifying the order may include a field that indicates whether the medication is chosen to be stored in the electronic medication storage cabinet or dispensed in some other manner.

If the one or more processors 202 determine that the ordered medication is chosen not be stored in the electronic medication storage cabinet (NO' at block 402), then the method 400 proceeds to block 403. At block 403, the one or more processors 202 determine that the medication will be dispensed as a patient specific medication (block 403). In some implementations, a user, such as a pharmacy technician, may specify for the ordered medication to be dispensed as a patient specific medication in electronic medication storage cabinet 104. In some implementations, a user, may provide an input to the electronic medication storage cabinet 104 to store the patient specific medication in electronic medication storage cabinet 104. For example, a user, when delivering the ordered medication, may desire to store the medication in the electronic medication storage cabinet 104 rather than in a different storage area, and may provide an input, to the electronic medication storage cabinet 104, to store the ordered medication in the electronic medication storage cabinet 104. In such implementations, in response to receiving such an input, the one or more processors 302 of the electronic medication storage cabinet 104 may be configured to transmit a message to the electronic medication storage system server 108 indicating that the ordered medication to be dispensed as patient specific medication, and the one or more processors 202 may initiate the method 400 from block 404.

Returning to block 402, if the one or more processors 202 determine that the ordered medication is chosen to be stored in the electronic medication storage cabinet 104, then the method proceeds to block 404. The one or more processors 202 determine whether the ordered medication can be stored in the electronic medication storage cabinet 104 (block 404). The processors 202 may be configured to determine, based on a set of predetermined rules stored in a memory of the electronic medication storage system server 108, whether the ordered medication can be stored in the electronic medication storage cabinet 104. For example, the set of predetermined rules may specify that a set of medications must be refrigerated, and the one or more processors 202 may be configured to determine that the ordered medication cannot be stored in the electronic medication storage cabinet 104 if the ordered medication is within the set of medications. Similarly, the set of predetermined rules may specify that certain types and/or classification of medications must be stored in a electronically controlled and/or managed storage tower, and the one or more processors 202 may be configured to determine that ordered medication cannot be stored in the electronic medication storage cabinet 104 if a type or a classification of the ordered medication matches one of the specified types or classifications.

If the one or more processors 202 determine that the ordered medication cannot be stored in the electronic medication storage cabinet 104 (NO' at block 404), then the method 400 proceeds to block 405-a. In some implementations, in response to the one or more processors 202 determining that the ordered medication cannot be stored in the electronic medication storage cabinet 104, the one or more processors 202 may be configured to generate and transmit an alert to medication system 110. The alert may indicate that the ordered medication cannot be loaded into the electronic medication storage cabinet 104, and may be configured to cause the generated alert to be provided and/or displayed to the user (e.g., on a display screen) by sending the alert to the medication system 110.

At block 405-a, the one or processors 202 determine whether the ordered medication can be refrigerated (block 405-a). As described above, the one or more processors 202 may be configured to determine whether a medication can be refrigerated based on a set of rules. If the one or more processors 202 determines that the medication can be refrigerated ('YES' at block 405-a), then the method 400 proceeds to block 405-b. The one or more processors 202 transmit a message to medication system 110 for storage of the ordered medication in a medication storage refrigerator (block 405-b). The one or more processors 202 may create steps to assist a user, such as a pharmacy technician, to load the ordered medication in the refrigerator and transmit the created steps and instructions to electronic medication storage cabinet 104. As described above, in some implementations, the electronic medication storage cabinet 104 may be associated with or communicatively coupled to an electronically controlled and/or managed refrigerator. The one or more processors 302 may be configured to provide and/or cause the created steps to be displayed on a display device associated with the electronic medication storage cabinet 104 for the user. For example, a user may scan the ordered medication and/or a package containing the ordered medication at the electronic medication storage cabinet 104, and the one or more processors 302 may be configured to provide the received created steps on a display device associated with the electronic medication storage cabinet 104.

Returning to block 405-a, if the one or more processors 202 determine that the ordered medication cannot be refrigerated ('NO' at block 405-a), then the method 400 continues to block 406-a. At block 406-a, the one or more processors 202 may be configured to determine whether the ordered medication can be stored in a tower configured to store medication (block 406-a). Similar to the refrigerator, in some implementations, the electronic medication storage cabinet 104 may be associated with and/or communicatively coupled to an electronically controlled and/or managed medication storage tower. If the one or more processors 202 determine that the ordered medication can be stored in the electronically controlled and/or managed medication storage tower ('YES' at block 406-*a*), then the method 400 proceeds to block 406-*b*. The processors 202 transmit a message to the medication system 110 for storage of the ordered medication in a medication storage tower (block 406-*b*). The one or more processors 202 may be configured to create and transmit steps and instructions to electronic medication storage cabinet 104 to assist a user to store the ordered medication in the electronically controlled and/or managed tower. If the one or more processors 202 determine that the ordered medication cannot be stored in the tower ('NO' at block 406-*a*), then the method 400 proceeds to the block 403. In some implementations, the one or more processors 202 may generate an alert that the ordered medication will have to be dispensed as a patient specific medication responsive to the one or more processors 202 determining that the ordered medication cannot be stored in the tower. The alert may be transmitted to the medication system 110.

Returning to block 404, if the one or more processors 202 determine that the ordered medication can be stored in the electronic medication storage cabinet 104 ('YES' at block 404), then the method 400 continues to block 408. The one or more processors 202 determine whether the ordered medication is a patient-specific medication (block 408). In some implementations, information specifying whether the ordered medication is a patient-specific medication is received by the electronic medication storage system server 108, and the one or more processors 202 may be configured to determine whether the ordered medication is a patient-specific medication based on the received information. For example, the message received from the medication system 110 may comprise information specifying whether the ordered medication is patient-specific or not, and the one or more processors 202 determine that the ordered medication is patient-specific based on the information in the message.

If the one or more processors 202 determine that the ordered medication is patient-specific ('YES' at block 408), then the method 400 continues to block 442. Additional details of the method 400 at block 442 are described herein with reference to FIG. 4C. If the one or more processors 202 determine that the ordered medication is not patient-specific ('NO' at block 408), then the method 400 continues to block 409. At block 409, the one or more processors 202 determine whether the electronic medication storage cabinet 104 at which the ordered medication can be loaded supports dynamic pockets (block 409). In some implementations, configuration data of the electronic medication storage cabinet 104 may specify whether the electronic medication storage cabinet 104 supports dynamic pockets, and the configuration data or information related to that configuration data may be stored in the electronic medication storage system server 108 (e.g., in a storage unit of and/or associated with the electronic medication storage system 108). The one or more processors 202 may be configured to determine whether the electronic medication storage cabinet 104 supports dynamic pockets based on the configuration data.

If the one or more processors 202 determine that the electronic medication storage cabinet 104 supports dynamic pockets ('YES' at block 409), then the method 400 continues to block 410. At block 410, the one or more processors 202 determine whether the ordered medication can be stored in a dynamic pocket of the electronic medication storage cabinet 104. As described above, an electronic medication storage cabinet 104 may include dynamic pockets, fixed pockets, and a combination thereof. The one or more processors 202 may be configured to determine whether medications can be stored in dynamic pockets based on a set of rules that specify whether certain medications are permitted to be stored in dynamic pockets. For example, the set of rules may specify a list of identifiers of medications that may only be stored in certain type of pockets of an automated drug dispensing cabinet 104, and the one or more processors 202 may be configured to check if an identifier of the ordered medication is within the list and determine that the ordered medication cannot be stored in a dynamic pocket if the identifier of the ordered medication is within that specified list. Similarly, the set of rules may specify that certain types of medications, such as controlled substances, may only be stored in secured pockets or pockets with a lid, such as a dynamic pocket in some implementations, and if the one or more processors 202 determines that the ordered medication is such a type of medication, then the processors 202 determine that the ordered medication can be stored in a dynamic pocket.

If the one or more processors 202 determine that the ordered medication may be stored in the dynamic pockets of the electronic medication storage cabinet 104, then the method 400 proceeds to block 411. The one or more processors 202 determine current locations of dynamic pockets in the electronic medication storage cabinet 104 (block 411). As described above, the pocket mapping module 242 may be configured to associate the dynamic and/or fixed pockets 130 of the electronic medication storage cabinet 104 with locations within the movable drawers 120. The one or more processors 202, via the pocket mapping module 242, may determine the locations of one or more dynamic pockets.

The one or more processors 202 determine a size of a dynamic pocket for the ordered medication (block 412). A user, such as a pharmacy technician, after reviewing the medication, may place the ordered medication in a dynamic pocket, referred to herein as an unassigned dynamic pocket. The unassigned dynamic pocket may be outside of the electronic medication storage cabinet 104 and not in any drawers 120 of the electronic medication storage cabinet 104. In some implementations, the electronic medication storage system server 108 may receive the size and/or dimensions of the unassigned dynamic pocket from the medication system 110.

The one or more processors 202 may associate the unassigned dynamic-pocket with the ordered medication. In some implementations, the electronic medication storage system server 108 may be configured to receive an identifier of the unassigned dynamic-pocket and an identifier of the ordered medication from the medication system 110, and the one or more processors 202 may be configured to associate the unassigned dynamic pocket with the ordered medication by associating the respective identifiers with each other. In some implementations, the one or more processors 202 may be configured to access medication system 110 to determine an identifier of the unassigned dynamic-pocket, and associate the ordered medication with the identifier of the unassigned dynamic-pocket. In some implementations, the electronic medication storage system server 108 may be configured with a set of rules that specify sizes and/or dimensions of dynamic pockets for various medications (e.g., identifiers of medications). The one or more processors 202, based on the ordered medication (e.g., identifier of the ordered medication) and the specified size and/or dimension of dynamic pocket in the set of rules, may be configured to determine size and/or dimensions of an unassigned dynamic pocket for the ordered medication.

The one or more processors 202 determines whether sufficient contiguous space is available in the electronic medication storage cabinet (block 413). In some implementations, the one or more processors 202, via pocket mapping module 242, may be configured to determine the dimensions of the movable drawers 120 of the electronic medication storage cabinets 104. In some implementations, the one or more processors 202, via pocket mapping module 242, may be configured to identify the locations in the electronic medication storage cabinet 104 that are not associated with any dynamic pockets, and calculate, based on the locations that are not associated with any dynamic pockets and dimensions of the movable drawers 120, the amount of contiguous space available in the electronic medication storage cabinet 104.

In some implementations, the one or more processors 202 may be configured to determine whether the calculated amount of contiguous space satisfies the dimensions and/or size of the unassigned dynamic pocket, and, if the calculated amount of contiguous space satisfies the dimensions and/or size of the unassigned dynamic pocket, then the one or more processors 202 may be configured to determine that sufficient contiguous space is available in the electronic medication storage cabinet 104. In some implementations, the one or more processors 202, may provide an alert to user (e.g., via a display device of the medication system 110) that indicates that the ordered medication can be stored in a dynamic pocket if the one or more processors 202 determine that sufficient contiguous free space is available for the unassigned dynamic pocket.

If the one or more processors 202 determine that sufficient contiguous space is available in the electronic medication storage cabinet 104 ('YES' at block 413), then the method 400 proceeds to block 414. At block 414, the one or more processors 202 transmit a message to the medication systems 110 indicating that the ordered medication can be dispensed in a dynamic pocket (block 414). In some implementations, the one or more processors 202 may be configured to specify instructions to dispense the ordered medications into the unassigned dynamic pocket. In some implementations, the one or more processors 202 may be configured to provide the medication system 110 access to an electronically controlled cabinet comprising dynamic pockets. In some implementations, the one or more processors 202 may identify a next available dynamic pocket for use by a user of the medication system 110 and transmit that information to the medication system 110.

In some implementations, the one or more processors 202, via the pocket mapping module 242, may be configured to assign one or more contiguous locations in the electronic medication storage cabinet 104 with the unassigned dynamic pocket. The one or more processors 202 create steps to place the unassigned dynamic pocket in the electronic medication storage cabinet 104 (block 415). The created steps may be sequential graphical steps. In some implementations, the one or more processors 202 generate an alert that the unassigned dynamic pocket is assigned space in the electronic medication storage cabinet 104. In some implementations, the one or more processors 202 may associate the created steps with the ordered medication and/or the unassigned dynamic pocket, and store the association in a storage unit of the electronic medication storage system server 108. The one or more processors 202 may be configured to transmit the created steps associated with an ordered medication and/or an unassigned dynamic pocket to electronic medication storage cabinet 104. As described below, the created steps may be displayed on a display device, such as display device 312, when the ordered medication is delivered to the electronic medication storage cabinet 104. Additional details of delivering an ordered medication to the electronic medication storage cabinet 104 are described herein in with reference to FIGS. 5A and 5B. The method 400 proceeds to block 490. The one or more processors 202 schedule the ordered medication for delivery to the electronic medication storage cabinet 104 (block 490). In some implementations, the one or more processors 202 may be configured to store data related to whether an ordered medication is successfully delivered to the electronic medication storage cabinet 104. In some implementations, the one or more processors 202 may transmit instructions to the electronic medication storage cabinet 104 indicating that an ordered medication is scheduled to be delivered to the electronic medication storage cabinet 104.

Returning to block 413, if the one or more processors 202 determine that sufficient contiguous space is not available ('NO' at block 413), then the method 400 proceeds to block 416. The one or more processors 202 determine whether any dynamic-pockets can be reorganized to create the sufficient contiguous space (block 416). For example, the one or more processors 202, via pocket arrangement module 246, may be configured to determine if sufficient contiguous space can be created in the electronic medication storage cabinet 104 by reorganizing or rearranging the one or more dynamic-pockets that are in the electronic medication storage cabinet 104. If sufficient contiguous space can be created by reorganizing the dynamic pockets, then the one or more processors 202 determine that dynamic-pockets can be reorganized. If the one or more processors 202 determine that one or more dynamic pockets can be reorganized to create sufficient contiguous space ('YES' at block 416), then the method 400 proceeds to block 417. At block 417, similar to block 414, the one or more processors 202 transmit a message to the medication system 110 indicating that the ordered medication can be dispensed or placed in a dynamic pocket.

The one or more processors 202 create steps to rearrange the dynamic-pockets (block 418). Similar to the created steps to place the unassigned dynamic pocket in the electronic medication storage cabinet 104, the created steps to rearrange the dynamic-pockets may be graphical, and the one or more processors 202, may be configured to transmit the created steps to the electronic medication storage cabinet 104. The one or more processors 202 create steps to place the unassigned dynamic pocket in the electronic medication storage cabinet 104 (block 419). The one or more processors 202 may be configured to transmit the created steps of placing the unassigned dynamic pocket in the electronic medication storage cabinet 104 to the electronic medication storage cabinet 104. The method 400 proceeds to block 490. The one or more processors 202 schedule the ordered medication for delivery to the electronic medication storage cabinet 104 (block 490).

Returning to block 416, if the one or more processors 202 determine that sufficient contiguous space is not available (NO' at block 416), then the method 400 proceeds to block 420. The one or more processors 202 determine whether contents of a dynamic pocket in the electronic medication storage cabinet 104 can be combined with contents of another dynamic pocket of in the electronic medication storage cabinet 104 (block 420). In some implementations, the one or more processors 202 may be configured to determine that contents of a first dynamic pocket can be combined with contents of another dynamic pocket if a unique identifier of the medication in the first dynamic pocket is the same as a unique identifier of the medication in another dynamic pocket. In some implementations, the one or more processors 202 may be configured to determine the unique identifier of a medication based on received data related to the medications from the medication systems 110 and/or electronic medication storage cabinet 104. The electronic medication storage system server 108 may receive data related to a medication and a pocket 130 in which it is placed in an electronic medication storage cabinet 104 and store the data in a storage unit associated with the electronic medication storage system server 108. Based on such data, the one or more processors 202 may be configured to determine the pockets that contain medications with the same identifiers.

If the one or more processors 202 determine that the contents of the dynamic pocket can be combined with contents of another dynamic pocket, then the method 400 proceeds to block 421. At block 421, similar to blocks 414 and 417, the one or more processors 202 transmit a message to the medication system 110 indicating that the ordered medication can be dispensed or placed in a dynamic pocket.

The one or more processors 202 create steps to combine dynamic pockets (block 422). For example, the one or more processors 202, via pocket mapping module 242, may be configured to create steps to combine medication of one dynamic-pocket with medication of another dynamic-pocket. The one or more processors 202 create steps to remove the freed or the empty dynamic-pocket in the electronic medication storage cabinet 104 (block 423). The one or more processors 202 create steps to place the unassigned dynamic-pocket in the electronic medication storage cabinet 104 (block 424). The one or more processors 302 may create steps to place the unassigned dynamic-pocket in a location of the freed dynamic pocket in the electronic medication storage cabinet 104. The method 400 proceeds to block 490. The one or more processors 202 schedule the ordered medication for delivery to the electronic medication storage cabinet 104 (block 490).

Returning to block 420, if the one or more processors 202 determine that the contents of a dynamic pocket in the electronic medication storage cabinet 104 cannot be combined with contents of another dynamic pocket of in the electronic medication storage cabinet 104 ('NO' at block 420), then the method 400 proceeds to block 425. The one or more processors 202 determine whether current inventory in any dynamic pockets can be removed. (block 425). To determine whether current inventory may be removed from pockets of the electronic medication storage cabinet 104, the one or more processors 202 may be configured to determine whether there are any patient-specific medications for patients who were transferred or discharged from the medical facility or a unit of medical facility (block 449 in FIG. 4D). In some implementations, each patient-specific medication may be associated with a patient for whom the medication is ordered. The associations may be stored in a storage unit associated with the electronic medication storage system server 108 and/or electronic medication storage cabinet 104. The one or more processors 202, based on the stored associations, may determine if any of the medications in the pockets are associated with transferred out or discharged patients.

If the one or more processors 202 determines that a pocket 130 in the electronic medication storage cabinet 104 includes medications for transferred or discharged patients ('YES' at block 449), then the method 400 proceeds to block 450. At block 450, the one or more processors 202 determine that the patient-specific medication can be removed. The one or more processors 202 may be configured to create steps for removal of patient-specific medication and transfer the steps to the electronic medication storage cabinet 104. If the one or more processors 202 determine that the electronic medication storage cabinet 104 does not include any patient-specific medications for transferred or discharged patients (NO' at block 449), then the method 400 proceeds to block 451. The one or more processors 202 determine whether any pockets in the electronic medication storage cabinet 104 include any discontinued medication (block 451). In some implementations, a set of rules may specify a list of patient-specific medication that are discontinued, and the one or more processors 202 may be configured to determine that a patient-specific medication in a pocket is discontinued if the medication matches a medication in the specified list.

If the one or more processors 202 determine that a pocket includes a discontinued medication ('YES' at block 451), then the method 400 proceeds to block 452. The one or more processors 202 determine that the patient-specific medication can be removed. The one or more processors 202, similar to block 450, may be configured to create steps for removal of patient-specific medication and transfer the steps to the electronic medication storage cabinet 104. If the one or more processors 202 determine that the discontinued medications are not stored in the electronic medication storage cabinet 104 ('NO' at block 451), then the method 400 proceeds to block 453. At block 453, the one or more processors 202 determine whether a medication in a pocket 130 of the electronic medication storage cabinet is a standard stock item. In some implementations, a set of rules may specify a list of medications that are predetermined to be standard stock type of medications, and the one or more processors 202 may determine if a medication in a pocket is standard stock based on the specified list of medications.

If the one or more processors 202 determine that the medication in the pocket 130 is of a standard stock type ('YES' at block 453), then the method 400 proceeds to block 458. The one or more processors 202 determine that the medication should not be removed from the electronic medication storage cabinet 104 (block 458). If the one or more processors 202 determine that the medication in the pocket is not of a standard stock type ('NO' at block 453), then the method 400 proceeds to block 454. The one or more processors 202 determine whether there are any active orders for a medication in a pocket 130 at an electronic medication storage cabinet 104 (block 454). In some implementations, the one or more processors 202 may store and update a list of current active orders and corresponding medications for the orders in a storage unit of the electronic medication storage cabinet 104. In some implementations, the one or more processors 202 may determine whether there are any active orders for a medication based on the stored list specifying the current active orders.

If the one or more processors 202 determine there is an active order for a medication ('YES' at block 454), then the proceeds to block 458, and the one or more processors 202 determine that the medication cannot be removed (block 458). If the one or more processors 202 determine there are no active orders for medications in any pocket 130 of the electronic medication storage cabinet 104 (NO' at block 454), then the method 400 proceeds to block 455. The one or more processors 202 determine if any of the medications are potentially expired in the electronic medication storage cabinet 104 (block 455). If the one or more processors 202 determine that there are medications that may be potentially expired in the electronic medication storage cabinet 104 ('YES' at block 455), then the method proceeds to block 456, and the one or more processors 202 determine that the expired medication can be removed. The one or more processors 202 may be configured to create steps to remove the expired medication from the electronic medication storage cabinet 104 and transmit the created steps to the electronic medication storage cabinet 104. If the one or more processors 202 determine that there are no medications in any pockets 130 of the electronic medication storage cabinet 104 that are potentially expired ('NO' at block 455), then the method 400 proceeds to block 457.

The one or more processors 202 determine if a medication in a pocket 130 has been withdrawn and/or used for a patient within a threshold number of days (block 457). The one or processors 202 may receive data for medications stored in electronic medication storage cabinets 104 that were used for patients and a date and time at which they were used, and based on such data, the one or more processors 202 may be configured to determine whether a medication in an electronic medication storage cabinet 104 has been withdrawn and/or used for a patient within the threshold number of days. If the one or more processors 202 determines that the medication in a pocket has been withdrawn and/or used within a threshold number of days ('YES' at block 457), then the method 400 proceeds to block 458, and the one or more processors 202 determines that the medication cannot be removed (block 458). If the one or more processors 202 determines that the medication in the pocket 130 has not been withdrawn and/or used within a threshold number of days ('NO' at block 457), then the method 400 proceeds to block 459. The one or more processors 202 determine that the medication in the pocket 130 can be removed (block 459).

Figure 4A:
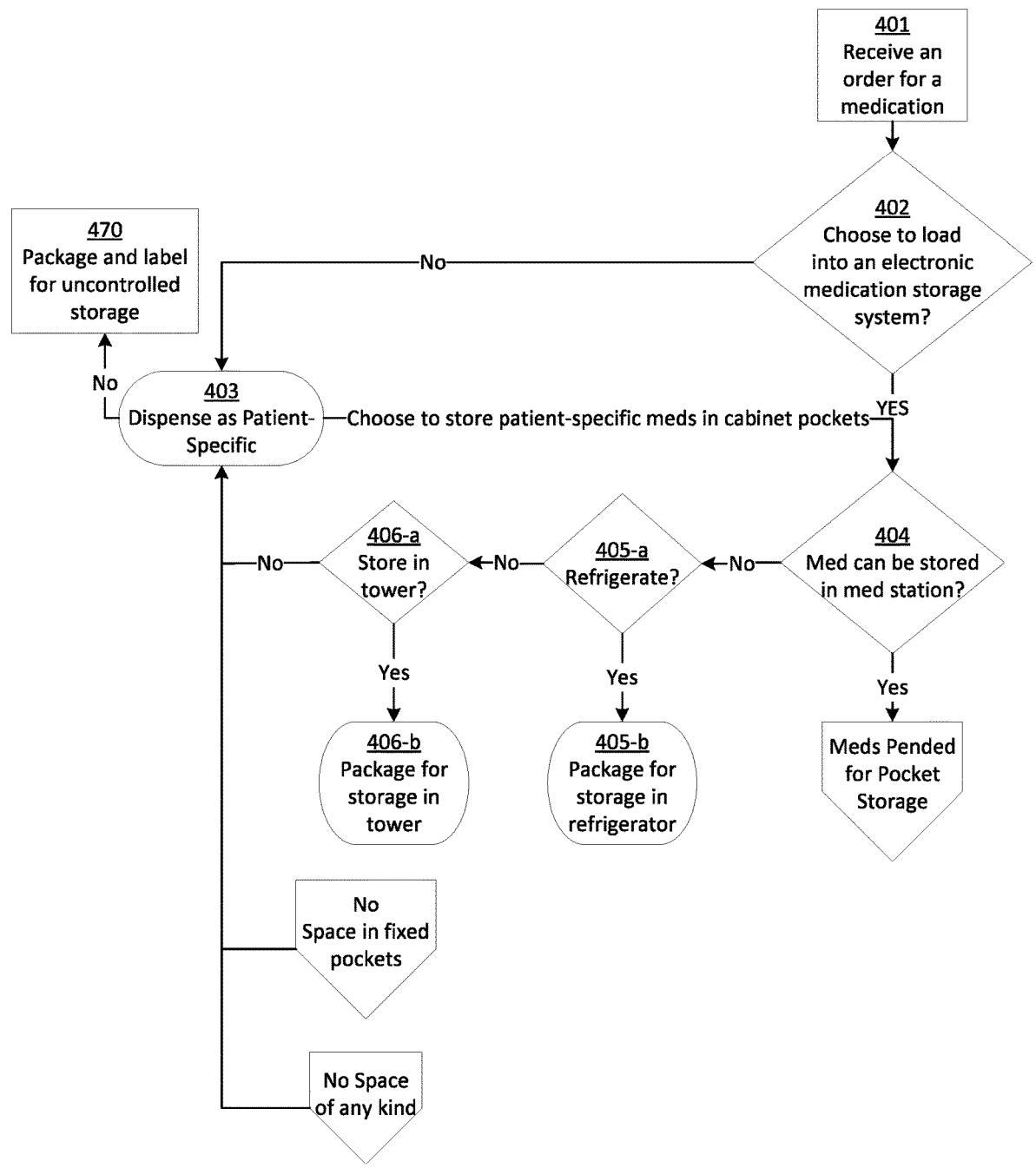
FIGS. 4A-4D are flow charts of an example method of identifying a location to store a medication into an electronic medication storage cabinet according to illustrative implementations.
Figure 4B:
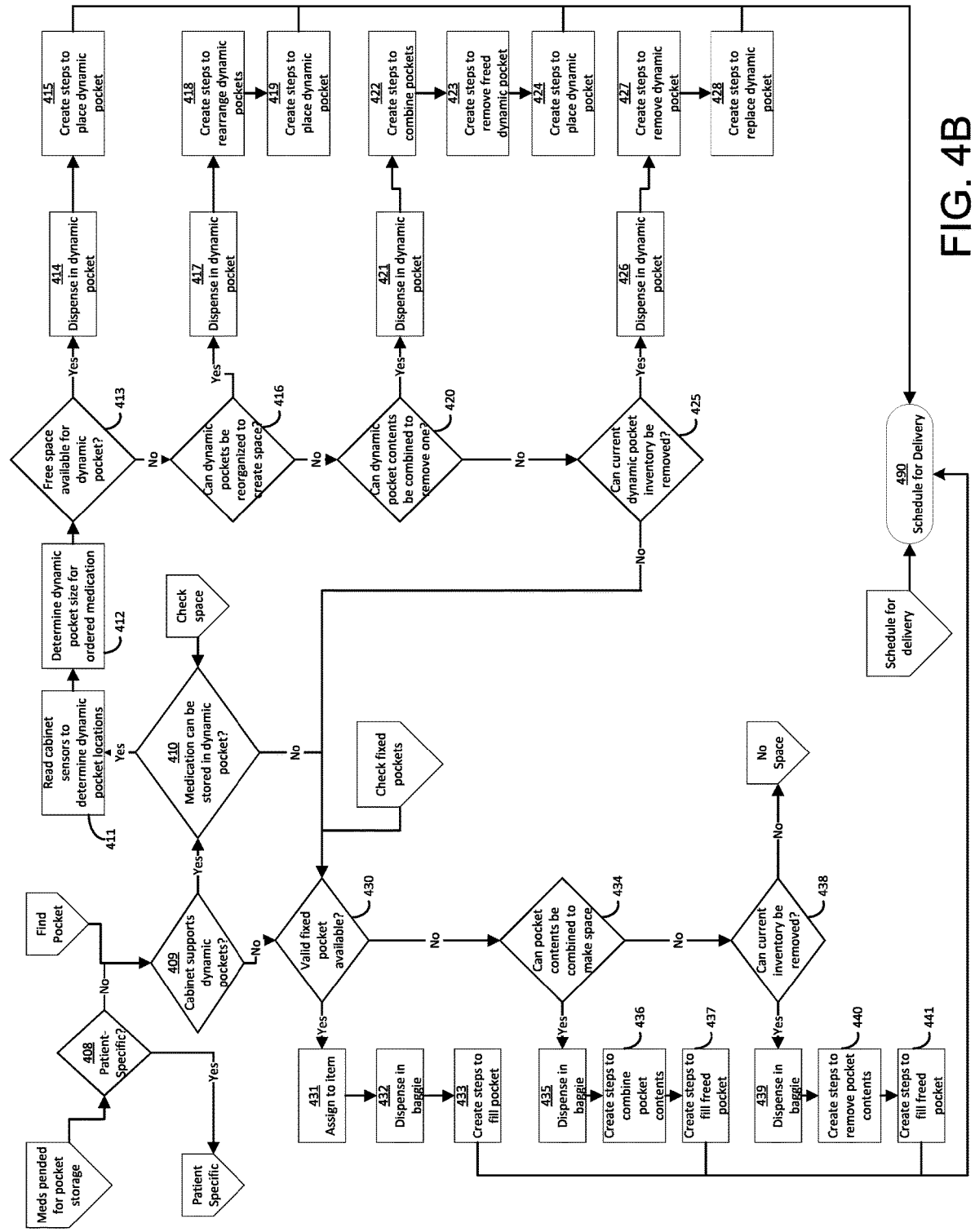

Returning to block 425 in FIG. 4B, if the one or more processors 202 determine that inventory in a dynamic pocket 130 can be removed ('YES' at block 425), then the method proceeds to block 426. At block 426, similar to blocks 414, 417, 421, the one or more processors 202 transmit a message to the medication system 110 indicating that the ordered medication can be dispensed or placed in a dynamic pocket.

The one or more processors 202 create steps to remove one or more dynamic pockets that include inventory (e.g., medications) that can be removed (block 427). The one or more processors 202 may transmit the created steps to remove the one or more dynamic pockets to the electronic medication storage cabinet 104. The one or more processors 202 create steps to place the unassigned dynamic pocket in the electronic medication storage cabinet 104 (block 428). The created steps may indicate that the unassigned dynamic pocket may be placed in the same location as the dynamic pocket that was removed. The one or more processors 202 may be configured to transmit to the electronic medication storage cabinet 104, the created steps to place the unassigned dynamic pocket in the electronic medication storage cabinet 104. The method 400 proceeds to block 490. The one or more processors 202 schedule the ordered medication for delivery to the electronic medication storage cabinet 104 (block 490).

Returning to block 425, if the one or more processors 202 determine that current inventory in any dynamic pockets 130 cannot be removed ('NO' at block 425), then the method proceeds to block 430. In some implementations, at block 425, if the one or more processors 202 determine that current inventory in any dynamic pockets 130 cannot be removed, then the one or more processors 202 may be configured to transmit a message to medication systems 110 indicating that the ordered medication cannot be dispensed and/or placed in a dynamic pocket in the electronic medication storage cabinet 104

Returning to block 410, if the one or more processors 202 determine that the medications cannot be stored in a dynamic pocket ('NO' at block 410), then the method 400 proceeds to block 430. And at block 409, if the one or more processors 202 determine that the electronic medication storage cabinet 104 does not support any dynamic pockets ('NO' at block 409), then the method 400 proceeds to block 430.

At block 430, the one or more processors 202 determine whether a valid fixed pocket is available. In some implementations, the one or more processors 202 may be configured to determine that a valid fixed-pocket is available if the list of empty pockets stored by the storage identification module 234 includes the fixed-pocket. If the one or more processors 202 determine that a valid fixed-pocket is available ('YES' at block 430), then the method proceeds to block 431. The one or more processors 202 assigns the valid-fixed pocket to the ordered medication (block 431). The one or more processors 202 may be configured to associate the ordered medication with the assigned valid fixed-pocket and store the mapping in a storage unit.

The one or more processors 202 transmit a message to the medication systems 110 indicating that the ordered medication can be dispensed in a baggie (block 432). The term "baggie" as used herein may be any type of a container to hold a medication. The one or more processors 202 create steps to fill the valid fixed-pocket (block 433). The one or more processors 202 may be configured to create the steps based on certain characteristics of the fixed pocket. For example, if the fixed pocket is configured with a lid, then the one or more processors 202 may create a step to open the lid and the close lid after the ordered is successfully placed in the pocket. Similarly, if the fixed pocket is an open pocket or without a lid, then the one or more processors 202 may be configured to not create a step for opening a lid. The one or more processors 202 may be configured to receive data related to such characteristics of pockets 130 from the electronic medication storage cabinets 104, and the one or more processors 202 may associate each pocket 130 with its corresponding characteristics and store the association in a storage unit associated with the electronic medication storage system server 108.

In some implementations, the created steps may be a sequence of graphical steps configured to instruct a user to fill the pocket in an appropriate manner. In some implementations, the one or more processors 202 may associate the created steps with the ordered medication, and store the association in a storage unit associated with the electronic medication storage system server 108. The one or more processors 202 may transmit the association and the created steps to the electronic medication storage cabinet 104. The one or more processors 202 may be configured to cause the display of the created steps associated with an ordered medication on a display device, such as display device 312 of the electronic medication storage cabinet 104, when the ordered medication is delivered to the electronic medication storage cabinet 104. The method 400 proceeds to block 490. The one or more processors 202 schedule the ordered medication for delivery to the electronic medication storage cabinet 104 (block 490). Additional details of delivering an ordered medication to the electronic medication storage cabinet are described herein in with reference to FIGS. 5A and 5B.

Returning to block 430, if the one or more processors 202 determine that a valid fixed pocket is not available ('NO' at block 430), then the method 400 proceeds to block 434. The one or more processors 202 determine whether contents of a fixed pocket can be combined with contents of another fixed pocket (block 434). The one or more processors 202 may be configured to determine that contents of a first fixed pocket can be combined with contents of another fixed pocket if a unique identifier of the medication in the first fixed pocket is the same as a unique identifier of the medication in another fixed pocket. As described above, in some implementations, the one or more processors 202 may be configured to determine the unique identifier of a medication based on received data related to the medications from the medication systems 110 and/or electronic medication storage cabinet 104. The one or more processors 202 may be configured to determine the pockets that contain medications with the same identifiers based on data related to a medication and a pocket 130 in which it is placed in an electronic medication storage cabinet 104.

If the one or more processors 202 determine that contents of a fixed pocket can be combined with contents of another fixed pocket ('YES' at block 434), then the method proceeds to block 435. The one or more processors 202 creates steps to instruct the user to dispense the ordered medication in a baggie (block 435). The one or more processors 202 creates steps to combine the contents from one fixed pocket with contents from another fixed pocket (block 436). The one or more processors 202 may be configured to create steps to combine inventory. In some implementations, the created steps may be a sequence of graphical steps configured to instruct a user to remove contents from a first pocket and store contents in a second pocket. In some implementations, the one or more processors 202 associate the freed fixed-pocket to the ordered medication. The one or more processors 202 create steps to fill the freed or empty fixed-pocket (block 437). The method 400 proceeds to block 490. The one or more processors 202 schedule the ordered medication for delivery to the electronic medication storage cabinet 104 (block 490).

At block 434, if the one or more processors 202 determine that the contents of a fixed-pocket cannot be combined with contents of another fixed-pocket (NO' at block 434), then the method 400 proceeds to block 438. The one or more processors 202 determine whether any of the current inventory in any fixed-pocket of the electronic medication storage cabinet 104 can be removed (block 438). As described above, the method proceeds to block 439 to determine whether current inventory may be removed from pockets of the electronic medication storage cabinet 104. If the one or more processors 202 determine that the current inventory cannot be removed ('NO' at block 438), then the one or more processors 202 determine and store an indicator in a storage unit (e.g., a flag in a register of a storage unit), which represents that for the ordered medication space in fixed pockets of an electronic medication storage cabinet 104 is not available. The method 400 proceeds to the block 403, and at block 403, the one or more processors 202 may be configured to determine if space in fixed pockets is available for this ordered medication based on the stored indicator. If the one or more processors 202 determines that the space in fixed pockets is not available for the ordered medication, then the method 400 proceeds to block 470. The one or more processors 202 determine that the ordered medication can be packaged and labeled for uncontrolled storage (block 470). The one or more processors 202 may transmit a message to the medication system 110 indicating that the ordered medication can be packaged and labelled for uncontrolled storage.

Returning to block 438, if the one or more processors 202 determine that the current inventory can be removed ('YES' at block 438), then the method 400 proceeds to block 439. The one or more processors 302 create steps to instruct the user to dispense the ordered medication in a baggie (block 439). The one or more processors 302 create steps to remove contents from a fixed-pocket (block 440). The one or more processors 302 create steps to fill the freed or empty pocket (block 441). The one or more processors 302 may associate the freed pocket with the ordered medication. The method 400 proceeds to block 490. The one or more processors 202 schedule the ordered medication for delivery to the electronic medication storage cabinet 104 (block 490).

Figure 4C:
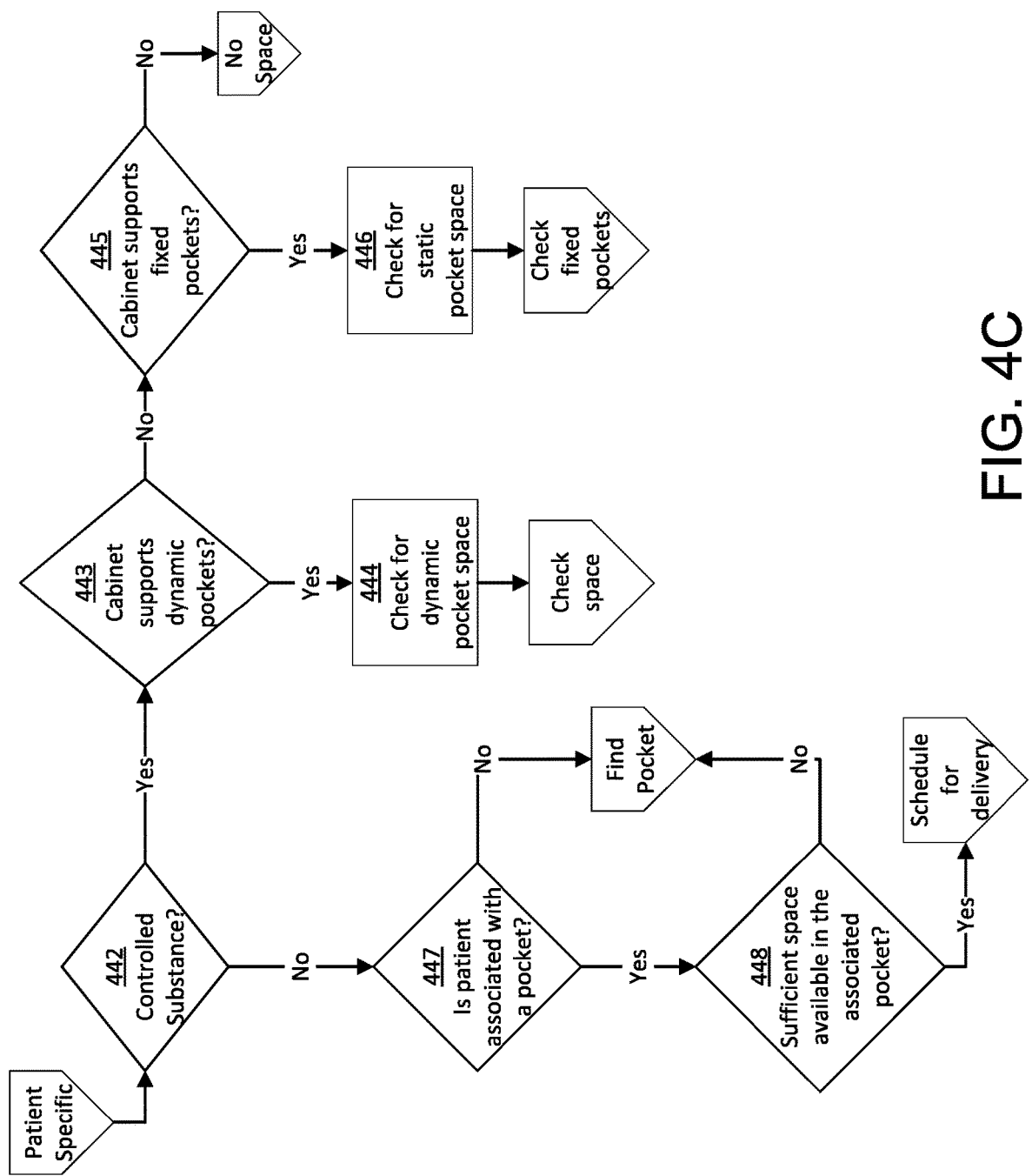

Returning to block 408, if the one or more processors 202 determine that the ordered medication is a patient-specific medication, then the method 400 proceeds to block 442, as shown in FIG. 4C. The one or more processors 202 determines whether the ordered medication is a controlled substance (block 442). In some implementations, the one or more processors 202 may determine if the ordered medication is a controlled substance based on a stored set of rules that specify a list of medications that are predetermined to be controlled substances. If the one or more processors 202 determine that the ordered medication is a controlled substance ('YES' at block 442), then the method proceeds to block 443. The one or more processors 202 determine whether the electronic medication storage cabinet 104 supports dynamic pockets (block 443). If the one or more processors 202 determine that the electronic medication storage cabinet 104 supports dynamic pockets ('YES' at block 443), then the method proceeds to block 444. The one or more processors 202 initiate the process of checking for available space in the dynamic pockets of the electronic medication storage cabinet 104 (block 444), and the method 400 proceeds to block 410.

If the one or more processors 202 determine that the electronic medication storage cabinet 104 does not support dynamic pockets ('NO' at block 443), then the method 400 proceeds to block 445. The one or more processors 202 determine whether the electronic medication storage cabinet 104 supports fixed-pockets (block 445). If the one or more processors 202 determine that the electronic medication storage cabinet 104 supports fixed-pockets ('YES' at block 445), then the method 400 proceeds to block 446. The one or more processors 202 initiate the process of checking for available space in fixed-pockets of the electronic medication storage cabinet 104 (block 446), and the method 400 proceeds to block 430. If the one or more processors 202 determine that the electronic medication storage cabinet 104 does not support fixed pockets, then the method 400 proceeds to block 403. In some implementations, if the one or more processors 202 determine that the electronic medication storage cabinet 104 does not support fixed pockets, then the one or more processors 202 determine and store an indicator in a storage unit (e.g., a flag in a register of a storage unit), which represents that space is unavailable in the pockets of the electronic medication storage cabinet 104. The method 400 proceeds to the block 403, and at block 403, the one or more processors 202 may be configured to determine if space in the pockets is available for the ordered medication based on the stored indicator. If the one or more processors 202 determines that the space in the pockets is unavailable for the ordered medication, then the method 400 proceeds to block 470.

At block 442, if the one or more processors 202 determine that ordered medication is not a controlled substance, then the method 400 proceeds to block 447. The one or more processors 202 determine whether the patient is associated with a particular pocket (block 447). As described above, the electronic medication storage system server 108 may receive data related to patients and pockets 130 of electronic medication storage cabinets 104, including associations between patients and one or more pockets 130 in an electronic medication storage cabinet 104. Based on the received data, the one or more processors 202 may determine whether the patient is associated with a pocket 130 in the electronic medication storage cabinet 104. If the one or more processors 202 determine that the patient is not associated with a pocket ('NO' at block 447), then the method 400 proceeds to block 409. If the one or more processors 202 determine that the patient is associated with a pocket ('YES' at block 447), then the method 400 proceeds to block 448. The one or more processors 202 determine whether sufficient space is available in the associated pocket (block 448). If the one or more processors 202 determine that sufficient space is not available in the associated pocket ('NO' at block 448), then the method 400 proceeds to block 409. If the one or more processors 202 determine that sufficient space is available in the associated pocket ('YES' at block 448), then the one or more processors 202 determine that the medication can be placed in the pocket 130 associated with the patient. The method 400 proceeds to block 490. The one or more processors 202 schedule the ordered medication for delivery to the electronic medication storage cabinet 104 (block 490).

Figure 4D:
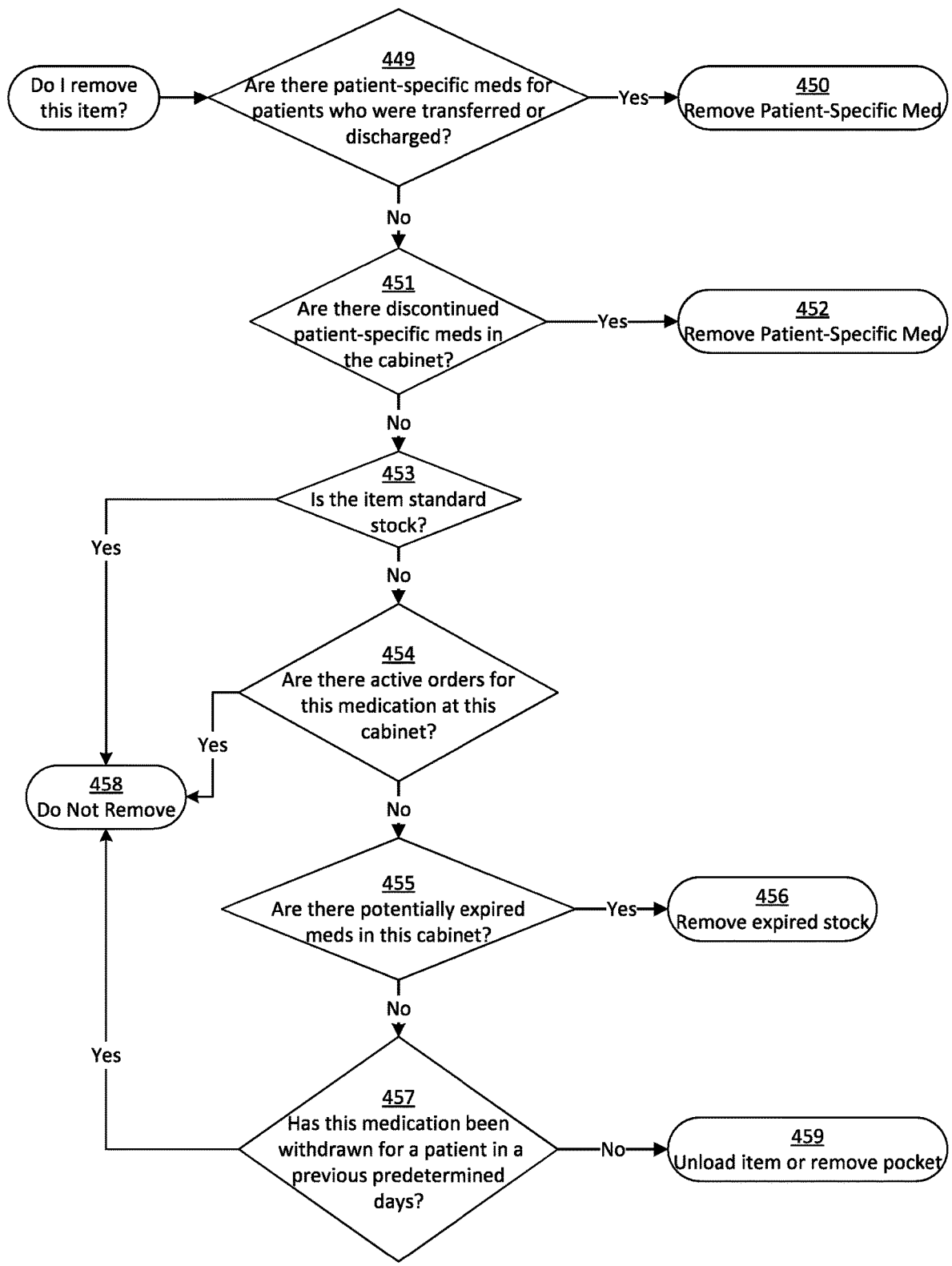
Figure 5A:
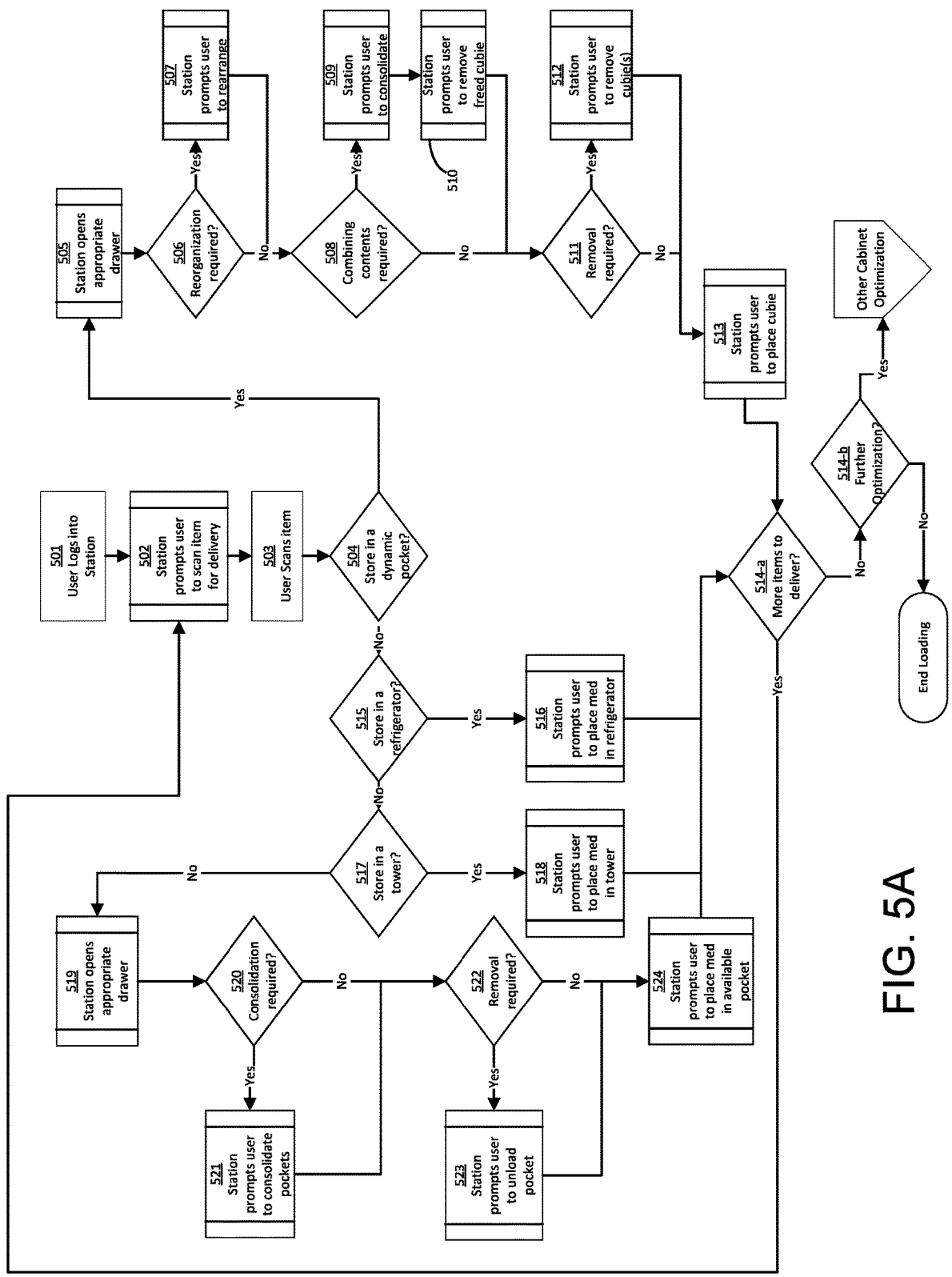
FIGS. 5A-5B are flow charts of an example method of loading a medication into an electronic medication storage cabinet, according to illustrative implementations.
Figure 5B:
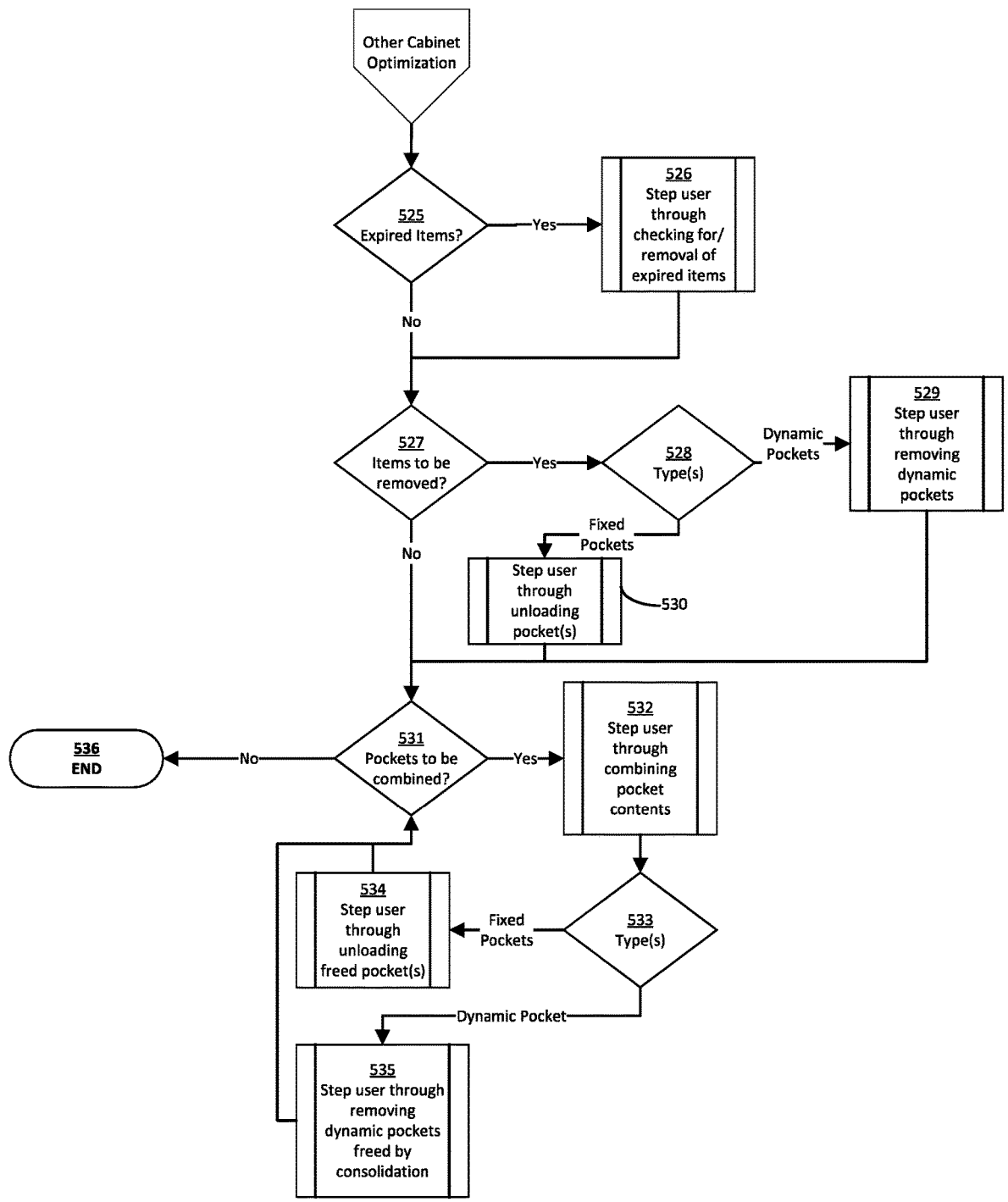

Turning now to FIGS. 5A-5B, there are shown flowcharts illustrating an optimized process of loading a medication in an electronic medication storage cabinet. For the purpose of illustrating a clear example, components of the network architecture 100, shown and described with reference to FIG. 1, components of the electronic medication storage system server 108, shown and described with reference to FIG. 2, and components of the electronic medication storage cabinet 104, shown and described with reference to FIG. 3, and processes described with reference to FIGS. 4A-4D may be used to describe the optimized process of loading a medication in an electronic medication storage cabinet.

The method 500 includes receiving, by one or more processors 302 of the electronic medication storage cabinet 104 (e.g., electronic medication storage cabinet 104-1), a user login information (block 501). The one or more processors 302 may be configured to determine whether the user is authorized user. The one or more processors 302 cause a prompt to be displayed on a display device (e.g., display device 312) associated with the electronic medication storage cabinet 104 for scan of an ordered medication (block 502). The one or more processors 302 receive information of the scanned medication (block 503). Based on the received information of the scanned medication, the one or more processors 302 determine whether the scanned medication can be placed in a dynamic pocket in the electronic medication storage cabinet 104 (block 504). The one or more processors 302 determine whether the scanned medication will be stored in a dynamic pocket based on information generated for the scanned medication based on the processes described with reference to FIGS. 4A-4D.

If the one or more processors 302 determine that the scanned medication will be loaded into a dynamic pocket ('YES' at block 504), then the method 500 proceeds to block 505. The one or more processors 302 cause the electronic medication storage cabinet 104 to open a movable drawer 120 in which the unassigned dynamic pocket containing the scanned medication will be placed (block 505). The one or more processors 302 may be configured to select a drawer 120 based on the steps created by the electronic medication storage system server 108 for the scanned medication based on the processes described with reference to FIGS. 4A-4D.

The one or more processors 302 determine if loading the scanned medication in the electronic medication storage cabinet 104 requires reorganization of one or more dynamic pockets of the electronic medication storage cabinet 104 (block 506). Based on the steps created by the electronic medication storage system server 108, the one or more processors 302 determine whether the reorganization of the one or more dynamic pockets is required. For example, if the electronic medication storage cabinet 104 has not received any data related to steps created for reorganizing one or more dynamic pockets, then the one or more processors 302 determine that reorganization of dynamic pockets are not required for loading the scanned medication in the electronic medication storage cabinet 104.

If the one or more processors 302 determine that loading the scanned medication in the electronic medication storage cabinet 104 requires reorganization of one or more dynamic pockets 130 ('YES' at block 506), then the method 500 proceeds to block 507. The one or more processors 302 provide the created steps to reorganize one or more dynamic pockets for display (block 507). The one or more processors 302 may provide the created steps for display on a display device associated with the electronic medication storage cabinet 104. The one or more processors 302 may provide the created steps in a sequence for display. For each of the created steps, the one or more processors 302 may be configured to determine whether the step is successfully completed. Additional details of determining whether the created steps are successfully completed are described below with reference to FIG. 6. The method proceeds to block 508.

If the one or more processors 302 determine that loading the scanned medication in the electronic medication storage cabinet 104 does not require reorganization of one or more dynamic pockets 130 ('NO' at block 506), then the method 500 proceeds to block 508. The one or more processors 302 determine whether loading the scanned medication in the electronic medication storage cabinet 104 require combining contents of one or more dynamic pockets (block 508). The one or more processors 302 may be configured to determine whether combining contents of one or more dynamic pockets with another pocket is required based on the set of created steps received for the scanned medication. If the received set of created steps do not indicate combining contents of dynamic pockets with other pockets, then the one or more processors 302 determine that combining contents of one or more dynamic pockets is not required for loading the scanned medication in the electronic medication storage cabinet 104. Similarly if the received set of created steps indicate combining contents of one or more dynamic pockets, then the one or more processors 302 determine that combining contents is not necessary for loading the scanned medication in the electronic medication storage cabinet 104.

If the one or more processors 302 determine that combining contents of one or more dynamic pockets is required for loading the scanned medication in the electronic medication storage cabinet 104 ('YES' at block 508) to place the unassigned pocket in the electronic medication storage cabinet 104, then the method 500 proceeds to block 509. At block 509, the one or more processors 302 cause display of the created steps to combine pockets. The one or more processors 302 cause display of created steps to remove the empty dynamic pocket (block 510). After the one or more processors 302 determine that the steps for combining pockets and removing empty pockets are successfully completed, the method 500 proceeds to block 511. The one or more processors 302 determines whether loading of the scanned medication require removal of any medications in the electronic medication storage cabinet 104 (block 511). If the one or more processors 302 determine that removal of medications is needed to load the scanned drug ('YES' at block 511), then the method 500 proceeds to block 512.

The one or more processors 302 cause display of created steps to remove contents from dynamic pockets of the electronic medication storage cabinet 104 (block 512), and the method 500 proceeds to block 513. The one or more processors 302 causes display of created steps to place the dynamic pocket in the electronic medication storage cabinet 104. The method 500 proceeds to block 514. At block 514, the one or more processors 302 determine whether there are any more medications to be delivered to the electronic medication storage cabinet 104. If the one or more processors 302 determine that there are additional medications to be delivered to the electronic medication storage cabinet 104 ('YES' at block 514-*a*), then the method 500 proceeds to block 502. If the one or more processors 302 determine that there are no additional medications to be delivered ('NO' at block 514-*b*), then the method 500 proceeds to block 514-*b*. The one or more processors 302 determine whether further optimization of the electronic storage cabinet 104 is desired (block 514-*b*). The one or more processors 302 may be configured to receive an input from a user of the electronic storage cabinet 104 indicating whether the user desires further optimization of the electronic storage cabinet 104. Based on the user input, if the one or more processors 302 determine that the further optimization is desired ('YES' at block 514-*b*), then the method 500 proceeds to block 525. Based on the user input, if the one or more processors 302 determine that further optimization is not desired (NO' at block 514-*b*), then the method 500 ends.

In some implementations, the one or more processors 302 may be configured to transmit a message to electronic storage server system 108 in response to determining that further optimization is desired, and the one or more processors 202 may be configured to determine further optimizations based on the process described with reference to FIG. 4D. In some implementations, the one or more processors 302 may be configured to determine optimizations of the electronic storage cabinet 104 based on the process described above in FIG. 4D.

At block 525, the one or more processors 302 determine whether any of the pockets of the electronic storage cabinet 104 include any expired medications. As described above, the one or more processors 302 may be configured to determine the contents of each pocket, and in some implementations, based on the contents, the one or more processors 302 may be configured to determine whether medication in a pocket has expired. If the one or more processors 302 determine that medications in pockets have not expired ('NO' at block 525), then the method 500 proceeds to block 527. If the one or more processors 302 determine that medication in a pocket has expired ('YES' at block 525), then the method 500 proceeds to block 526. The one or more processors 302 provide, for display, steps generated for removal of the expired items (block 526). After the one or more processors 302 determine that the steps generated for removal of the expired items are successfully completed, the method 500 proceeds to block 527.

The one or more processors 302 determine whether other contents of pockets can be removed (block 527). In some implementations, the one or more processors 302 may be configured to determine whether contents of a pocket will be removed based on determining whether any of the pockets have medications for discharged patients. Additional details of removing medications of discharged patients are described above with reference to FIG. 4D. If the one or more processors 302 determine that other contents of pockets do not have to be removed ('NO' at block 527), then the method proceeds to block 531. If the one or more processors 302 determine that other contents of pockets can be combined ('YES' at block 527), then the method 500 proceeds to block 528. The one or more processors 302 determine a type of the pocket from which contents can be removed (block 528).

If the one or more processors 302 determine that the pocket is a dynamic pocket ('Dynamic Pocket' at block 528), then the method 500 proceeds to block 529. The one or more processors 302 provide for display steps generated to remove the dynamic pocket (block 529). After the one or more processors 302 determine that the steps for removing the dynamic pockets were successfully completed, then the method 500 proceeds to block 531. If the one or more processors 302 determine that the pocket is a fixed pocket ('Fixed Pocket' at block 528), then the method 500 proceeds to block 530. The one or more processors 302 provide for display steps generated to remove contents from the fixed pocket (block 529) After the one or more processors 302 determine that the steps for removing the contents from the fixed pocket were successfully completed, then the method 500 proceeds to block 531.

The one or more processors 302 determine whether contents of any pockets may be combined (block 531). The one or more processors 302 may be configured to combine medications of one pocket with another pocket if the medications in the two pockets have the same unique identifier. If the one or more processors 302 determine that the contents of the pockets may not be combined ('NO' at block 531), then the method 500 ends. If the one or more processors 302 determine that the contents of pockets may be combined ('YES' at block 531), then the method 500 proceeds to block 532. The one or more processors 302 provide for display steps generated for combining contents of one pocket with another pocket (block 532). The one or more processors 302 determine a type of the pocket (block 533).

If the one or more processors 302 determine that the type of the pocket is a fixed pocket ('Fixed Pockets' at block 533), then the method 500 proceeds to block 534. The one or more processors 302 provide for display steps generated to unload freed pocket (block 534). After the one or more processors 302 confirm that the steps are successfully completed, the method 500 proceeds block 531. If the one or more processors 302 determine that the type of the pocket is dynamic pocket ('Dynamic Pockets' at block 534), then the method 500 proceeds to block 535. The one or more processors 302 provide for display steps generated to remove the freed dynamic pocket. After the one or more processors 302 confirm that the steps are successfully completed, the method 500 proceeds block 531. At block 531, when the one or more processors 302 determine that no pockets can be combined ('NO' at block 531), then the method 500 ends.

Returning block 504, if the one or more processors 302 determine scanned medication will not be stored in the dynamic pocket (NO' at block 504), then the method 500 proceeds to block 515. The one or more processors 302 determine whether the scanned medication should be refrigerated (block 515). If the one or more processors determine that the scanned medication should be refrigerated ('YES' at block 515), then the method 500 proceeds to block 516. The one or more processors 302 cause display of a prompt to place the scanned medication in the refrigerator. If the one or more processors 302 determine that the scanned medication should not be refrigerated (NO' at block 515), then the method proceeds to block 517. The one or more processors 302 determine whether the scanned medication should be placed in a tower (block 517). If the one or more processors 302 determine that the scanned medication should be placed in the tower ('YES' at block 517), then the method 500 proceeds to block 518. The one or more processors 302 cause the display of a prompt to a user to place the scanned medication in the tower (block 518).

If the one or more processors 302 determine that the scanned medication should not be placed in tower ('NO' at block 517), then the method 500 proceeds to block 519. The one or more processors 302 cause a drawer of the electronic medication storage cabinet 104 to be opened. The opened drawer may include one or more fixed pockets. The method 500 proceeds to block 520, and at block 520, the one or more processors 302 determine whether loading of the scanned medication will require contents of any fixed pocket to be combined with contents of another fixed pocket. If the one or more processors 302 determine that the contents will need to be combined ('YES' at block 520), then the method proceeds to block 521. The one or more processors 302 cause display of the created steps to combine contents of one fixed pocket with contents of another fixed pocket (block 521). The method 500 proceeds to block 522. At block 520, if the one or more processors 302 determine that the contents of one fixed pocket are not required to be combined with contents of another fixed pocket (NO at block 520), then the method proceeds to block 522.

The one or more processors 302 determines whether removal of any contents of any fixed pockets is required for loading scanned medication (block 522). If the one or more processors 302 determine that removal is needed ('YES' at block 522), then the method proceeds to block 523. The one or more processors 302 causes display of the created steps to remove contents of a fixed pocket (block 523), and the method proceeds to block 524. If the one or more processors 302 determine that removal is not needed ('NO' at block 522), then the method proceeds to block 524. At block 524, the one or more processors 302 cause display of the created steps to place the scanned medication into the freed or empty pocket. The method continues to block 514.

In some implementations, the one or more processors 302 determine whether a step of the created steps is successfully completed. In some implementations, the one or more processors 302 may be configured to determine that a current step of the created steps is successfully completed based on data from one or more sensors of the electronic medication storage cabinet. For example, if the current step requires placing a pocket 130 in a certain location of the drawer 120 of the electronic medication storage cabinet 104, the processor 302 may be configured to determine whether pocket was placed in the correct location based on the data from sensors associated with that location that indicate that the pocket was placed in that location.

In some implementations, if the processor 302 determines that a current step is not successfully completed then the one or more processors 302 may be configured to generate a remedial step. The one or more processors 302 may be configured to generate the remedial step based on user inputs. For example, if the one or more processors 302, via the one or more sensor devices, determine that the pocket is placed in a location different from the expected location, then the processor 302 may be configured to generate a remedial step that corrects the error by providing instructions to remove the pocket from that location. The one or more processors 302 may cause the remedial step to be displayed. The one or more processors 302 may determine whether the remedial step is successfully completed. For example, the one or more processors 302 may be configured to determine that the remedial step of removing the pocket from the wrong location is successfully completed based on data from sensors associated with that location.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software, or any combination thereof.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method, comprising: providing an electronic medication storage cabinet comprising a plurality of drawers, each drawer configured with a plurality of storage pockets, the drawer configured with a plurality of sensors arranged to identify a positioning of the plurality of storage pockets within the drawer; receiving an indication of a new medicine container to be loaded in the electronic medication storage cabinet; displaying a first step of a sequence of one or more steps to load the medicine container into an electronic medication storage cabinet on a display on the electronic medication storage cabinet, wherein the sequence is generated based on a mapping algorithm; determining whether the first step of the sequence of the one or more steps is associated with one of the plurality of drawers; in response to determining that the first step is associated with one of the plurality of drawers, automatically unlocking the associated drawer; determining whether the first step is successfully completed; in response to determining that the first step is successfully completed, determining whether execution of any additional steps is pending; and generating an alert in response to determining that execution of no additional steps is pending.

Clause 2. The method of Clause 1, further comprising: providing, on the display, a first prompt to remove a first storage pocket from a first location within the plurality of drawers, wherein first prompt is associated with the first step; verifying, via the plurality of sensors, that the first storage pocket is removed; and in response to verifying that the first storage pocket is removed, determining that the first step is successfully completed.

Clause 3. The method of Clause 2, further comprising: in response to determining that execution of at least one additional step is pending, transitioning to a next pending step in the sequence of the one or more steps; providing, on the display, a second prompt to relocate the first storage pocket within a first available space within the plurality of drawers, wherein the second prompt is associated with the next pending step; and verifying, via the plurality of sensors, that the first storage pocket was relocated to the first available space.

Clause 4. The method of Clause 3, further comprising: in response to verifying that the first storage pocket was relocated to the first available space, determining that the next pending step is successfully completed; transitioning to a subsequent pending step in the sequence of the one or more steps; and providing, on the display, a third prompt to insert a new storage pocket within a second available space within the plurality of drawers, wherein the third prompt is associated with the subsequent pending step.

Clause 5. The method of Clause 1, further comprising: in response to determining that the first step is not successfully completed, generating a remedial step; and displaying the remedial step on the display.

Clause 6. The method of Clause 5, further comprising: determining whether the remedial step is successfully completed; and in response to the remedial step being successfully completed, displaying the first step of the sequence of the one or more steps on the display.

Clause 7. The method of Clause 1, further comprising: prior to automatically unlocking the associated drawer, requesting authorized credentials to access the electronic medication storage cabinet; and receiving an indication authorizing access to the electronic medication storage cabinet.

Clause 8. The method of Clause 1, wherein the plurality of sensors are arranged in a grid pattern in the drawer.

Clause 9. The method of Clause 1, wherein one or more of the plurality of sensors are arranged in a perimeter around the inside of the drawer.

Clause 10. The method of Clause 1, wherein the alert is a visual alert.

Clause 11. A method, comprising: providing a electronic medication storage cabinet comprising a plurality of drawers, each drawer configured with a plurality of removable storage pockets, the drawer configured with a plurality of sensors arranged to identify a positioning of the plurality of removable storage pockets within the drawer; receiving an indication of a new medicine container to be stored in the electronic medication storage cabinet requires a new storage pocket to be added to the electronic medication storage cabinet; determining, based on receiving the indication, that at least a subset of removable storage pockets within one or more of the plurality of drawers require repositioning to accommodate the new pocket; generating, based on a mapping algorithm, a new arrangement of the subset of removable storage pockets and the new pocket within the one or more of the plurality of drawers; executing, at the electronic medication storage cabinet, a predetermined sequence of steps for effecting the new arrangement, comprising: automatically unlocking a first drawer of the plurality of drawers; providing a first prompt to remove at least a first storage pocket of the subset of removable storage pockets; verifying, via the plurality of sensors, that the first storage pocket was removed; providing a second prompt to relocate the first pocket within a first available space within the one or more of the plurality of drawers; verifying, via the plurality of sensors, that the first pocket was relocated; providing a third prompt to insert the new pocket within a second available space of the one or more of the plurality of drawers; verifying, via the plurality of sensors, that the new pocket was inserted.

Clause 12. The method of Clause 11, wherein, prior to providing the third prompt, the executing further comprises: automatically unlocking a second drawer of the plurality of drawers; providing a fourth prompt to remove at least a second storage pocket of the subset of removable storage pockets; verifying, via the plurality of sensors, that the second storage pocket was removed; providing a fifth prompt to relocate the second pocket into a second available space within the one or more of the plurality of drawers; verifying, via the plurality of sensors, that the second pocket was relocated.

Clause 13. The method of Clause 11, wherein, prior to automatically unlocking the first drawer; requesting access authorization verification; and receiving an indication authorizing access to the electronic medication storage cabinet.

Clause 14. The method of Clause 11, wherein, prior to automatically unlocking the first drawer; requesting access authorization verification; receiving an indication of limited access to the electronic medication storage cabinet; and generating, based on the mapping algorithm and the received indication of limited access, a second arrangement of the subset of removable storage pockets.

Clause 15. The method of Clause 14, further comprising: executing, at the electronic medication storage cabinet, a second predetermined sequence of steps for effecting the second arrangement, comprising: automatically unlocking a second drawer of the plurality of drawers; providing a fourth prompt to remove at least a second storage pocket of the subset of removable storage pockets; verifying, via the plurality of sensors, that the second storage pocket was removed; providing a fifth prompt to relocate the second pocket within a second available space within the one or more plurality of drawers; verifying, via the plurality of sensors, that the second pocket was relocated; providing a third prompt to insert the new pocket within the one or more of the plurality of drawers; verifying, via the plurality of sensors, that new first pocket was inserted.

Clause 16. A system, comprising: a memory storing instructions; and one or more processors coupled with the memory and configured to execute the instructions to cause the system to perform the steps of the method in claim 1.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiments described herein as "exemplary" is not necessarily to be construed as preferred or advantageous over other embodiments.

In one or more aspects, the terms "about," "substantially," and "approximately" may provide an industry-accepted tolerance for their corresponding terms and/or relativity between items.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method, comprising:
providing an electronic medication storage cabinet comprising a plurality of drawers and a plurality of sensors configured to identify a positioning of a plurality of storage pockets within the plurality of drawers;
receiving an indication of a new storage pocket associated with a new medicine container to be loaded in the electronic medication storage cabinet;
generating a sequence of steps to load the new storage pocket into the electronic medication storage cabinet, the generated sequence of steps including moving a first storage pocket of the plurality of storage pockets from a first location in a respective drawer of the storage cabinet to a second location in the storage cabinet to create sufficient space within the respective drawer for the new storage pocket;
displaying, on a display screen associated with the electronic medication storage cabinet, a first step of the sequence of steps, including a first prompt to remove the first storage pocket from the first location;
automatically unlocking the respective drawer;
determining that the first storage pocket is removed from the first location based on first signals received from the plurality of sensors of the respective drawer; and
in response to determining that the first storage pocket is removed, indicating via the display screen, a second prompt to place the first storage pocket in a second location within the plurality of drawers.

2. The method of claim 1, further comprising:
providing, on the display, the first prompt to remove the first storage pocket from the first location within a first drawer of the plurality of drawers;
in response to verifying that the first storage pocket is removed, providing the second prompt to relocate the first storage pocket to the second location in a second drawer of the plurality of drawers.

3. The method of claim 2, further comprising:
verifying, via the plurality of sensors, that the first storage pocket was relocated to the second location.

4. The method of claim 3, further comprising:
providing, on the display, a third prompt to insert a new storage pocket within a second available space within the plurality of drawers, wherein the third prompt is associated with a subsequent pending step.

5. The method of claim 1, further comprising:
in response to determining that the moving step is not successfully completed, generating a remedial step; and
displaying the remedial step on the display.

6. The method of claim 5, further comprising:
determining whether the remedial step is successfully completed; and
in response to the remedial step being successfully completed, displaying the moving step of the sequence of steps on the display.

7. The method of claim 1, further comprising:
prior to automatically unlocking the respective drawer, requesting authorized credentials to access the electronic medication storage cabinet; and
receiving an indication authorizing access to the electronic medication storage cabinet.

8. The method of claim 1, wherein the plurality of sensors are arranged in a grid pattern in the respective drawer, wherein verifying that the first storage pocket is removed comprises receiving a signal indicating that the first storage pocket was removed from one of the sensors, in the grid pattern, corresponding to the first location.

9. The method of claim 1, wherein one or more of the plurality of sensors are arranged in a perimeter around the inside of the respective drawer.

10. The method of claim 1, wherein indicating via the display screen whether any additional steps are pending comprises providing a visual alert on the display screen.

11. A method, comprising:
providing an electronic medication storage cabinet comprising a plurality of drawers and a plurality of sensors configured to identify a positioning of a plurality of storage pockets within the drawer;

receiving, by one or more processors, an indication of a new medicine container to be stored in the electronic medication storage cabinet;

automatically determining, by the one or more processors, that the new medicine container requires a new storage pocket to be added to the electronic medication storage cabinet;

determining, by the one or more processors, based on receiving the indication and determining that the new medicine container requires a new storage pocket, that at least a subset of removable storage pockets within one or more of the plurality of drawers require repositioning to accommodate the new storage pocket;

generating, by the one or more processors, based on a mapping algorithm, a new arrangement of the subset of removable storage pockets and the new storage pocket within the one or more of the plurality of drawers;

generating, based on the new arrangement, a sequence of steps to load the new storage pocket into the electronic medication storage cabinet, the generated sequence of steps including moving a first storage pocket of the plurality of storage pockets from a first location in a respective drawer of the plurality of drawers to a second location in the storage cabinet to create an available space within the respective drawer for the new storage pocket;

automatically unlocking, by the one or more processors, a first drawer of the plurality of drawers;

providing, by the one or more processors, a first prompt to remove at least the first storage pocket from the first location in the respective drawer;

verifying, by the one or more processors, via the plurality of sensors, that the first storage pocket was removed from the first location;

providing, responsive to verifying that the first storage pocket was removed, a second prompt to relocate the first storage pocket within a first available space to a second location within the one or more of the plurality of drawers;

verifying, by the one or more processors, via the plurality of sensors, that the first storage pocket was relocated;

providing, by the one or more processors, responsive to verifying that the first storage pocket was removed and relocated, a third prompt to insert the new storage pocket within the available space created for the new storage pocket in the respective drawer based on the removal and relocation of the first storage pocket;

verifying, by the one or more processors, via the plurality of sensors, that the new storage pocket was inserted within the available space.

12. The method of claim 11, wherein, prior to providing the third prompt, the method further comprises:

automatically unlocking a second drawer of the plurality of drawers;

providing a fourth prompt to remove at least a second storage pocket of the subset of removable storage pockets;

verifying, via the plurality of sensors, that the second storage pocket was removed;

providing a fifth prompt to relocate the second storage pocket into a second available space within the one or more of the plurality of drawers;

verifying, via the plurality of sensors, that the second storage pocket was relocated.

13. The method of claim 11, wherein, prior to automatically unlocking the first drawer;

requesting access authorization verification; and receiving an indication authorizing access to the electronic medication storage cabinet.

14. The method of claim 11, wherein, prior to automatically unlocking the first drawer;

requesting access authorization verification;

receiving an indication of limited access to the electronic medication storage cabinet; and generating, based on the mapping algorithm and the received indication of limited access, a second arrangement of the subset of removable storage pockets.

15. The method of claim 14, further comprising:

executing, at the electronic medication storage cabinet, a predetermined sequence of steps for effecting the second arrangement, comprising:

automatically unlocking a second drawer of the plurality of drawers;

providing a fourth prompt to remove at least a second storage pocket of the subset of removable storage pockets;

verifying, via the plurality of sensors, that the second storage pocket was removed;

providing a fifth prompt to relocate the second storage pocket within a second available space within the plurality of drawers;

verifying, via the plurality of sensors, that the second storage pocket was relocated;

providing a third prompt to insert the new storage pocket within the one or more of the plurality of drawers;

verifying, via the plurality of sensors, that new first pocket was inserted.

16. A system, comprising:

a memory storing instructions; and one or more processors coupled with the memory and configured to execute the instructions to cause the system to perform operations comprising:

receiving an indication of a new storage pocket associated with a new medicine container to be loaded in an electronic medication storage cabinet, the electronic medication storage cabinet comprising a plurality of drawers and a plurality of sensors configured to identify a positioning of a plurality of storage pockets within the plurality of drawers;

generating a sequence of steps to load the new storage pocket into the electronic medication storage cabinet, the generated sequence of steps including moving a first storage pocket of the plurality of storage pockets from a first location in a respective drawer of the storage cabinet to a second location in the storage cabinet to create sufficient space within the respective drawer for the new storage pocket;

displaying, on a display screen associated with the electronic medication storage cabinet, a first step of the sequence of steps, including a first prompt to remove the first storage pocket from the first location;

automatically unlocking the respective drawer;

determining that the first storage pocket is removed from the first location based on first signals received from the plurality of sensors of the respective drawer; and in response to determining that the first storage pocket is removed, indicating via the display screen, a second prompt to place the first storage pocket in a second location within the plurality of drawers.

17. The system of claim 16, wherein the operations further comprise:
- providing, on the display, the first prompt to remove the first storage pocket from the first location within a first drawer of the plurality of drawers;
- in response to verifying that the first storage pocket is removed, providing the second prompt to relocate the first storage pocket to the second location in a second drawer of the plurality of drawers.

18. The system of claim 17, wherein the operations further comprise:
- verifying, via the plurality of sensors, that the first storage pocket was relocated to the second location.

19. The system of claim 18, wherein the operations further comprise:
- providing, on the display, a third prompt to insert a new storage pocket within a second available space within the plurality of drawers, wherein the third prompt is associated with a subsequent pending step.

20. The system of claim 16, wherein the plurality of sensors are arranged in a grid pattern in the respective drawer, and wherein the operations further comprise:
- prior to automatically unlocking the respective drawer, requesting authorized credentials to access the electronic medication storage cabinet; and
- receiving an indication authorizing access to the electronic medication storage cabinet, wherein verifying that the first storage pocket is removed comprises receiving a signal indicating that the first storage pocket was removed from one of the sensors, in the grid pattern, corresponding to the first location.

* * * * *